US010309035B2

(12) United States Patent
Fujita et al.

(10) Patent No.: US 10,309,035 B2
(45) Date of Patent: Jun. 4, 2019

(54) METHOD OF PREPARING SAMPLE FOR CRYSTAL STRUCTURE ANALYSIS, METHOD OF DETERMINING ABSOLUTE CONFIGURATION OF CHIRAL COMPOUND, AND POLYNUCLEAR METAL COMPLEX MONOCRYSTAL

(71) Applicant: The University of Tokyo, Tokyo (JP)

(72) Inventors: Makoto Fujita, Tokyo (JP); Yasuhide Inokuma, Tokyo (JP); Tatsuhiko Arai, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 201 days.

(21) Appl. No.: 15/124,897

(22) PCT Filed: Mar. 9, 2015

(86) PCT No.: PCT/JP2015/056871
§ 371 (c)(1),
(2) Date: Sep. 9, 2016

(87) PCT Pub. No.: WO2015/137288
PCT Pub. Date: Sep. 17, 2015

(65) Prior Publication Data
US 2017/0016138 A1 Jan. 19, 2017

(30) Foreign Application Priority Data
Mar. 10, 2014 (JP) .................................. 2014-046706

(51) Int. Cl.
*G01N 1/28* (2006.01)
*G01N 23/207* (2018.01)
*C30B 7/14* (2006.01)
*C30B 29/54* (2006.01)
*C30B 7/06* (2006.01)

(52) U.S. Cl.
CPC ................. *C30B 7/06* (2013.01); *C30B 7/14* (2013.01); *C30B 29/54* (2013.01); *G01N 1/28* (2013.01); *G01N 23/207* (2013.01); *G01N 2223/60* (2013.01)

(58) Field of Classification Search
CPC .......... G01N 1/28; G01N 23/207; C30B 7/14; C30B 29/54; C30B 7/06
See application file for complete search history.

(56) References Cited

U.S. PATENT DOCUMENTS

| 2003/0008406 A1 | 1/2003 | Inoue et al. |
| 2010/0324249 A1 | 12/2010 | Fujita et al. |
| 2011/0098414 A1 | 4/2011 | Fujita et al. |

FOREIGN PATENT DOCUMENTS

| JP | 2001-220392 A | 8/2001 |
| JP | 2001-261613 A | 9/2001 |
| JP | 2003-207444 A | 7/2003 |
| JP | 2004-85279 A | 3/2004 |
| WO | 2007/102594 A1 | 9/2007 |

OTHER PUBLICATIONS

Inokunna et al., Nature, Mar. 28, 2013, vol. 495, pp. 461-466.*
International Search Report dated May 26, 2015, issued in counterpart International Application No. PCT/JP2015/056871 (2 pages).
Saito, "Zettai Haichi to Rittai Kagaku", Journal of the Crystallographic Society of Japan, 1977, vol. 19, No. 2, pp. 173-177, cited in ISR (5 pages).
Inokuma, Y. et al, "X-ray Analysis on the Nanogram to Microgram Scale Using Porous Complexes", Nature, Mar. 2013, vol. 495, No. 7442, pp. 461-466; cited in EESR.
Extended (supplementary) European Search Report dated Sep. 1, 2017, issued in counterpart European No. 15762396.8. (6 pages).

\* cited by examiner

*Primary Examiner* — Sun Jae Yoo
(74) *Attorney, Agent, or Firm* — Westerman, Hattori, Daniels & Adrian, LLP

(57) ABSTRACT

Method for preparing a crystal structure analysis sample for determining an absolute configuration of a chiral compound includes bringing a single crystal of a porous compound into contact with a solvent solution that contains a chiral compound, the single crystal of the porous compound including a three-dimensional framework, and either or both of pores and voids that are defined by the three-dimensional framework, and are three-dimensionally arranged in an ordered manner, the three-dimensional framework being formed by one molecular chain or two or more molecular chains, or formed by one molecular chain or two or more molecular chains, and a framework-forming compound, and comprising a chiral substituent of which the absolute configuration is known, the crystal structure analysis sample having a structure in which molecules of the chiral compound are arranged in either or both of the pores and the voids of the single crystal in an ordered manner.

5 Claims, 7 Drawing Sheets

(a)          (b)

(c)          (d)

METHOD OF PREPARING SAMPLE FOR CRYSTAL STRUCTURE ANALYSIS, METHOD OF DETERMINING ABSOLUTE CONFIGURATION OF CHIRAL COMPOUND, AND POLYNUCLEAR METAL COMPLEX MONOCRYSTAL

TECHNICAL FIELD

The present invention relates to a method for preparing a crystal structure analysis sample that is useful for determining the absolute configuration of a chiral compound, a method for determining the absolute configuration of a chiral compound that utilizes a crystal structure analysis sample obtained using the method for preparing a crystal structure analysis sample, and a single crystal of a polynuclear metal complex that is suitably used when implementing the method for preparing a crystal structure analysis sample.

BACKGROUND ART

When a chiral compound is used as a drug, an agricultural chemical, a fragance, or the like, there may be a case where only one of the enantiomers of the chiral compound exhibits the intended effect, or causes a side effect. Therefore, it is very important to determine the absolute configuration of a compound that is used as a drug, an agricultural chemical, a fragrance, or the like, or a raw material compound that is used to produce such a compound.

A method that utilizes circular dichroic spectroscopy and a method that utilizes nuclear magnetic resonance spectroscopy are known as a method for determining the absolute configuration of a chiral compound.

For example, Patent Literature 1 discloses a method that determines the absolute configuration of a chiral compound having a basic group that can be coordinated to a metal ion by coordinating the basic group to a metal ion of a metalloporphyrin having a specific structure, and measuring the circular dichroic spectrum of the product.

Patent Literature 2 discloses a method that determines the absolute configuration of an optically active alcohol by reacting a carboxyl group-containing optically active compound having a specific structure with an optically active alcohol or the like, and measuring the nuclear magnetic resonance spectrum of the resulting ester derivative or the like.

However the methods disclosed in Patent Literature 1 and 2 can only be applied to a chiral compound having a specific structure (coordinating atom or reactive group) from which a compound suitable for measurement can be derived.

A heavy atom method that utilizes the anomalous dispersion effect due to a heavy atom when implementing X-ray crystal structure analysis, and a method that introduces a chiral auxiliary (of which the absolute configuration is known) into the molecule of as chiral compound through an ionic bond or a covalent bond, and determines the absolute configuration of the chiral compound from the relative positional relationship with the chiral auxiliary, are known as a method for determining the absolute configuration of a chiral compound.

However, known X-ray crystal structure analysis has the following problems.

Specifically, it is necessary to prepare a high-quality single crystal when implementing X-ray crystal structure analysis. In order to prepare a high-quality single crystal, it is necessary to repeat a number of experiments through trial and error so as to determine optimum crystallization conditions. Therefore, X-ray crystal structure analysis is not necessarily efficient for determining the absolute configuration of a chiral compound.

It is normally necessary to provide at least several milligrams of sample (specimen) when conducting studies With regard to the crystallization conditions. Therefore, it is practically impossible to determine the absolute configuration of a chiral compound using X-ray crystal structure analysis when only a trace amount of chiral compound is available.

CITATION LIST

Patent Literal

Patent Literature 1: JP-A-2001-220392 (US2003/0008406A1)
Patent Literature 2: JP-A-2001-261613

SUMMARY OF INVENTION

Technical Problem

The invention was conceived in view of the above situation. An object of the invention is to provide a method for efficiently preparing a crystal structure analysis sample that is useful for determining the absolute configuration of a chiral compound, a method for determining the absolute configuration of a chiral compound that utilizes a crystal structure analysis sample obtained using the method for preparing a crystal structure analysis sample, and a single crystal of a polynuclear metal complex that is suitably used for the method for preparing a crystal structure analysis sample.

Solution to Problem

The inventors conducted extensive studies in order to solve the above technical problem. As a result, the inventor found that, when a single crystal of a porous compound (haying a three-dimensional framework that includes a chiral substituent of which the absolute configuration is known, and pores that are defined by the three-dimensional framework, and are three-dimensionally arranged in an ordered manner) is brought into contact With a solvent solution that includes a chiral compound for which the absolute configuration is to be determined, to obtain a single crystal of an inclusion complex in which the chiral compound is arranged in the pores of the single crystal in an ordered manner, and crystal structure analysis is performed using the resulting single crystal, it is possible to easily determine the absolute configuration of the chiral compound from the relative positional relationship with the chiral substituent. This finding has led to the completion of the invention.

Several aspects of the invention provide the following method for preparing a crystal structure analysis sample (see (1) to (5)), and method for determining the absolute configuration of a chiral compound (see (6)).

(1) A method for preparing a crystal structure analysis sample for determining the absolute configuration of a chiral compound, the method including bringing a single crystal of a porous compound into contact with a solvent solution that includes a chiral compound for which the absolute configuration is to be determined, to prepare a crystal structure analysis sample, the single crystal of the porous compound including a three-dimensional framework, and either or both of pores and voids that are defined by the three-dimensional framework, and are three-dimensionally arranged in an ordered manner, the three-dimensional framework being formed by one molecular chain or two or more molecular chains, or formed by one molecular chain or two or more molecular chains, and a framework-forming compound, and including a chiral substituent of which the absolute configuration is known, the crystal structure analysis sample having a structure in which molecules of the chiral compound are arranged in either or both of the pores and the voids of the single crystal in an ordered manner.

(2) The method kg preparing a crystal structure analysis sample according to (1), wherein the porous compound is a polynuclear metal complex that includes a ligand having two or more coordinating moieties, a metal ion that serves as a center metal, and the framework-forming compound that includes the chiral substituent of which the absolute configuration is blown.

(3) The method for preparing a crystal structure analysis sample according to (2), wherein the ligand having two or more coordinating moieties is a tridentate ligand represented by the following formula (1),

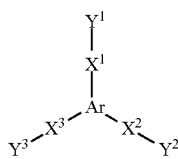
(1)

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety.

(4) The method for preparing a crystal structure analysis sample according to (2), wherein the metal ion that serves as the center metal is an ion of a metal among the metals that respectively belong to Groups 8 to 12 in the periodic table.

(5) The method for preparing a crystal structure analysis sample according to (1), wherein the single crystal is brought into contact with the solvent solution that includes the chiral compound by immersing the single crystal in the solvent solution that includes the chiral compound.

(6) A method for determining the absolute configuration of a chiral compound including determining the absolute configuration of a chiral compound by crystal structure analysis using a crystal structure analysis sample obtained using the method for preparing a crystal structure analysis sample according to any one of (1) to (5):

(7) A single crystal of a polynuclear metal complex including a tridentate ligand represented by the following formula (1), a metal ion that serves as a center metal, and a framework-forming compound that includes a chiral substituent of which the absolute configuration is known,

(1)

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety, wherein the chiral substituent of which the absolute configuration is known is a group among groups represented by the following formulas,

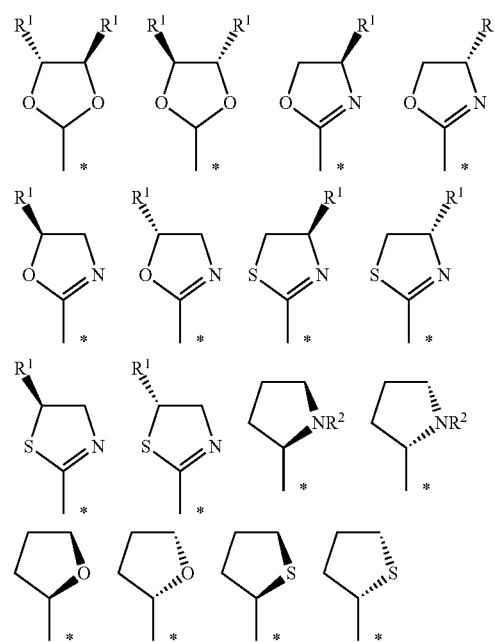

wherein $R^1$ is an alkyl group having 1 to 5 carbon atoms, $R^2$ is a hydrogen atom or an alkyl group having 1 to 5 carbon atoms, the alkyl group having 1 to 5 carbon atoms that is or may be represented by $R^1$ and $R^2$ being a methyl group, an ethyl group, or the like, and "*" represents the bonding position.

Advantageous Effects of Invention

Several aspects of the invention this provide a method for preparing a crystal structure analysis sample that is useful for determining the absolute configuration of a chiral compound, a method for determining the absolute configuration of a chiral compound that utilizes a crystal structure analysis sample obtained using the method for preparing a crystal structure analysis sample, and a single crystal of a polynuclear metal complex that is suitably used for the method for preparing a crystal structure analysis sample.

DESCRIPTION OF EMBODIMENTS

Figure 1:
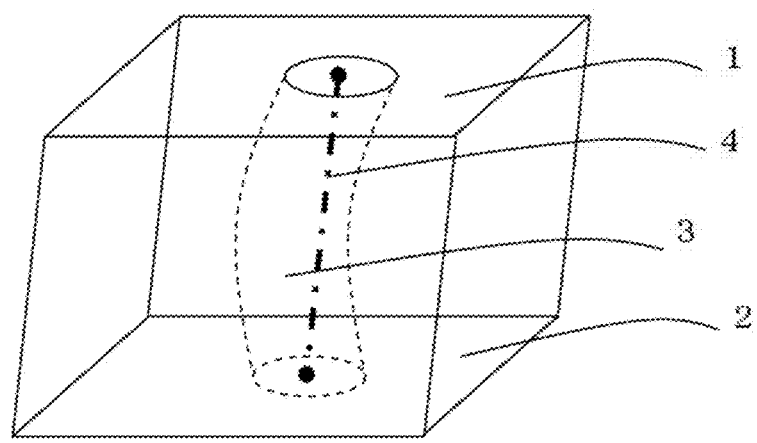
FIG. 1 is a view illustrating the extension direction of a pore that is formed in a single crystal.

A method for preparing a crystal structure analysis sample, a single crystal of a polynuclear metal complex, and a method for determining the absolute configuration of a chiral compound according to the exemplary embodiments of the invention are described in detail below.

1) Method for Preparing Crystal Structure Analysis Sample

A method for preparing a crystal structure analysis sample according to one embodiment of the invention prepares a crystal structure analysis sample for determining the absolute configuration of a chiral compound, the method including bringing a single crystal of a porous compound into contact with a solvent solution that includes a chiral compound for which the absolute configuration is to be determined, to prepare the crystal structure analysis sample, the single crystal of the porous compound including a three-dimensional framework, and either or both of pores and voids that are defined by the three-dimensional framework, and are three-dimensionally arranged in an ordered manner, the three-dimensional framework being formed by one molecular chain or two or more molecular chains, or formed by one molecular chain or two or more molecular chains, and a framework-forming, compound, and including a chiral substituent of which the absolute configuration is known, the crystal structure analysis sample having a structure in which molecules of the chiral compound are arranged in either or both of the pores and the voids of the single crystal in an ordered manner.

(i) Chiral Compound for Which Absolute Configuration is to be Determined

The method for preparing a crystal structure analysis sample according to one embodiment of the invention prepares a crystal structure analysis sample that is useful when determining the absolute configuration of a chiral compound (hereinafter may be referred to as "chiral compound (A)") by crystal structure analysis.

The chiral compound (A) is a compound having such a property (chirality) that the molecular structure thereof does not coincide with the molecular structure of its enantiomer (e.g., has a right hand-left hand relationship with its enantiomer). Examples of the chiral compound (A) include a compound that has a chiral center (center of asymmetry) in the molecule, a compound that has axial chirality or planar chirality in the molecule, and the like.

The term "absolute configuration" used herein refers to the spatial arrangement of each atom that forms a molecule of a chiral (optically active) compound.

The size of the chiral compound (A) is not particularly limited as long as the chiral compound (A) has a size that allows the chiral compound (A) to enter either or both of the pores and voids of the single crystal. The molecular weight of the chiral compound (A) is normally 20 to 3,000, and preferably 100 to 2,000.

It is also preferable to roughly determine the molecular size of the chiral compound (A) in advance by nuclear magnetic resonance spectroscopy, mass spectrometry, elemental analysis, or the like, and appropriately select a single crystal having appropriate pores and voids.

(ii) Solvent Solution that Includes Chiral Compound for which Absolute Configuration is to be Determined The solvent used to prepare the solvent solution that includes the chiral compound (A) is not particularly limited as long as the solvent does not dissolve the single crystal, and dissolves the chiral compound (A).

When concentrating the solvent solution that includes the chiral compound (A) by volatilizing the solvent from the solvent solution that includes the chiral compound (A) (as described later), it is preferable to use a solvent having a boiling point at normal pressure ($1 \times 10^5$ Pa) of 200° C. or less, more preferably −50 to 185° C., and still more preferably 30 to 80° C.

Specific examples of the solvent include an aromatic hydrocarbon such as benzene, toluene, xylene, chlorobenzene, 1,2-dichlorobenzene, and nitrobenzene; an aliphatic hydrocarbon such as n-butane, n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide (DMSO); an amide such as N,N-dimethylformamide and N-methylpyrrolidone; an ether such as diethyl ether, tetrahydrofuran, 1,2-dimethoxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

Among these, an aromatic hydrocarbon such as benzene, toluene, xylene, chlorobenzene, and 1,2-dichlorobenzene, an alicyclic hydrocarbon such as cyclopentane, cyclohexane, and cycloheptane, a nitrile such as acetonitrile and benzonitrile, and the like are preferable.

The solvent solution that includes the chiral compound (A) includes the chiral compound (A) in an amount of 5 mg or less, preferably 0.5 μg to 1 mg, and more preferably 1 μg to 0.5 mg, for example.

When determining the compound crystallization conditions using a known crystallization method, it is necessary to provide at least about 5 mg of sample. However, the method for preparing a crystal structure analysis sample according to one embodiment of the invention can easily prepare a crystal structure analysis sample even when the content of the chiral compound (A) is 5 mg or less (i.e., even when it is difficult to obtain a single crystal using a known crystallization method).

The concentration of the chiral compound (A) in the solvent solution (that includes the chiral compound (A)) is not particularly limited. The concentration of the chiral compound (A) in the solvent solution is normally 0.001 to 50 μg/μL, preferably 0.01 to 5 μg/μL, and more preferably 0.1 to 1 μg/μL, from the viewpoint of efficiently preparing a high-quality crystal structure analysis sample.

The solvent solution that includes the chiral compound (A) may be purified using a known purification method before implementing the method for preparing a crystal structure analysis sample according to one embodiment of the invention. Examples of the purification method include centrifugation, filtration, dialysis, solvent extraction, electrophoresis, liquid chromatography, and the like. These purification methods may be used either alone or in combination.

(iii) Single Crystal of Porous Compound

The single crystal of the porous compound used in connection with one embodiment of the invention includes a three-dimensional framework, and either or both of pores and voids that are defined by the three-dimensional framework, and are three-dimensionally arranged in an ordered manner, the three-dimensional framework being formed by one molecular chain or two or more molecular chains, or formed by one molecular chain or two or more molecular chains, and a framework-forming compound, and including a chiral substituent of which the absolute configuration is known.

The term "three-dimensional framework" used herein refers to a framework-like structure that three-dimensionally extends within the single crystal. The three-dimensional framework is formed by one molecular chain or two or more molecular chains, or formed by one molecular chain or two or more molecular chains, and a framework-forming compound.

The term "molecular chain" used herein refers to an assembly that is formed by means of either or both of a covalent bond and a coordinate bond. The molecular chain may include a branched structure and a cyclic structure.

Examples of the three-dimensional framework that is formed by one molecular chain include a framework that is assembled in the form of a jungle gym.

The term "three-dimensional framework that is formed by two or more molecular chains" used herein refers to a framework in which two or more molecular chains are assembled (connected or bonded) by means of a hydrogen bond, a π-π stacking interaction, a Van der Waals force, or the like. Examples of the three-dimensional framework that is formed by two or more molecular chains include a framework in which two or more molecular chains are intertwined in the form of a puzzle ring. Specific examples of such a three-dimensional framework include the three-dimensional framework of the polynuclear metal complex 1 and the three-dimensional framework of the polynuclear metal complex 2 (described later).

The term "framework-forming compound" used herein refers to a compound that does not form part of a molecular chain, but forms part of a three-dimensional framework by means of a hydrogen bond, a π-π stacking interaction, a Van der Waals force, or the like. Examples of the framework-forming compound include the framework-forming aromatic compound included in the polynuclear metal complex described later.

The expression "either or both of pores and voids that are three-dimensionally arranged in an ordered manner" means that either or both of the pores and the voids are arranged in an ordered manner to such an extent that either or both of the pores and the voids can be observed by crystal structure analysis.

The terms "pore" and "void" used herein refer to an internal space within the single crystal. More specifically the internal space within the single crystal that extends in the form of a tube is referred to as "pore", and the internal space within the single crystal that does not extend in the form of a tube is referred to as "void".

The size of each pore has a correlation with the diameter of a circle that is inscribed to the pore (hereinafter may be referred to as "pore inscribed circle") in a plane parallel to the crystal plane that is closest to a perpendicular plane with respect to the extension direction of the pore (hereinafter may be referred to as "parallel plane"). The diameter of the pore inscribed circle increases as the size of the pore increases, and decreases as the size of the pore decreases.

"The extension direction of the pore" may be determined as described below.

Specifically, a crystal plane X (e.g., plane A, plane B, plane C, or diagonal plane thereof) that extends in an appropriate direction that intersects the target pore is selected. The atoms that are present in the crystal plane X and included in the three-dimensional framework are represented using the van der Waals radius to draw a cross-sectional view of the pore taken along the crystal plane X. Likewise, a cross-sectional view of the pore taken along a crystal plane Y that is shifted from the crystal plane X by one unit cell is drawn. The center of the cross-sectional shape of the pore in the crystal plane X and the center of the cross-sectional shape of the pore in the crystal plane Y are connected using a straight line (dash-dotted line) (see FIG. 1). The direction in which the straight line extends corresponds to the extension direction of the pore.

"The diameter of the pore inscribed circle" may be determined as described below.

Specifically a cross-sectional view of the pore taken along the parallel plane is drawn in the same manner as described above. The pore inscribed circle is drawn using the cross-sectional view, and the diameter of the pore inscribed circle is measured. The measured value is converted to the actual scale to determine the actual diameter of the pore inscribed circle.

The diameter of the pore inscribed circle in each parallel plane is measured while subjecting the parallel plane to a gradual parallel shift by one unit cell to determine the diameter of the smallest inscribed circle and the diameter of the largest inscribed circle.

The diameter of the pore inscribed circle of the single crystal used in connection with one embodiment of the invention is preferably 2 to 30 Å, and more preferably 3 to 1.0 Å.

When the shape of the pore significantly differs from a true circle, it is preferable to predict the inclusion capability of the single crystal from the minor axis and the major axis of the pore inscribed ellipse (i.e., the ellipse that is inscribed to the pore) in the parallel plane.

The major axis of the pore inscribed ellipse of the single crystal used in connection with one embodiment of the invention is preferably 2 to 30 Å, and more preferably 3 to 10 Å. The minor axis of the pore inscribed ellipse of the single crystal used in connection with one embodiment of the invention is preferably 2 to 30 Å, and more preferably 3 to 10 Å.

The pore volume in the single crystal used in connection with one embodiment of the invention may be calculated using the method described in Acta Crystallogr. A46, 194-201 (1990). Specifically, the pore volume in the single crystal may be calculated using the expression "volume of single crystal×void ratio in unit cell" based on solvent accessible voids (void volume in unit cell) calculated by a calculation program. (PLATON SQUEEZE PROGRAM).

The pore volume in the single crystal used in connection with one embodiment of the invention (i.e., the total pore volume in one piece of the single crystal) is preferably $1\times10^{-7}$ to 0.1 mm$^3$, and more preferably $1\times10^{-5}$ to $1\times10^{-3}$ mm$^3$.

When the single crystal has voids, the size of each void may be calculated using the method described in Acta Crystallogr. A46, 194-201 (1990) in the same manner as the pore volume.

It is preferable that the single crystal used in connection with one embodiment of the invention be in the shape of a cube or a rectangular parallelepiped. The dimension of one side of the single crystal used in connection with one embodiment of the invention is preferably 10 to 1,000 µm, and more preferably 60 to 200 µm. A high-quality crystal structure analysis sample can be easily obtained by utilizing a single crystal having a shape and a size as described above.

It is preferable that the single crystal used in connection with one embodiment of the invention be designed so that the molecular structure can be determined at a resolution of at least 1.5 Å when MoKα radiation (wavelength: 0.71 Å) generated at a tube voltage of 24 kV and a tube current of 50 mA is applied to the single crystal, and the diffracted X-rays are detected using a CCD detector. A high-quality crystal structure analysis sample can be easily obtained by utilizing a single crystal having such properties.

The three-dimensional framework includes a chiral substituent of which the absolute configuration is known (hereinafter may be referred to as "substituent (a)"). Note that a plurality of substituents (a) are included in the three-dimensional framework, and are arranged in an ordered manner. The presence of the plurality of substituents (a) can be determined by crystal structure analysis.

A three-dimensional framework that includes the substituent (a) may be formed by utilizing a multidentate ligand that includes the substituent (a), a framework-forming compound that includes the substituent (a), or the like as a three-dimensional framework-forming material (as described later). It is considered that the absolute configuration of the substituent (a) does not change through the formation of a three-dimensional framework.

The type and the size of the substituent (a) are not particularly limited as long as the substituent (a) does not clog either or both of the pores and the voids of the single crystal (i.e., does not hinder inclusion of the chiral compound (for which the absolute configuration is to be determined) in either or both of the pores and the voids of the single crystal). The number of carbon atoms of the substituent (a) is preferably 1 to 100, more preferably 2 to 60, and still more preferably 3 to 20.

A group having a cyclic structure is preferable as the substituent (a) from the viewpoint of suppressing a situation in which the crystal structure is disordered, and availability. It is preferable that the group having a cyclic structure include a 3 to 7-membered ring, more preferably a 4 to 6-membered ring, and still more preferably a 5-membered ring.

Examples of the substituent (a) having a cyclic structure include groups respectively represented by the following formulas.

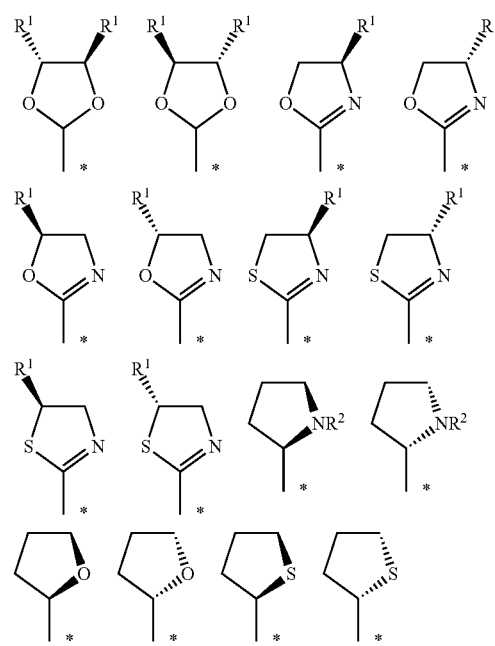

wherein R$^1$ is an alkyl group having 1 to 5 carbon atoms, and R$^2$ is a hydrogen atom or an alkyl group having 1 to 5 carbon atoms. Examples of the alkyl group having 1 to 5 carbon atoms that is (may be) represented by R$^1$ and R$^2$ include a methyl group, an ethyl group, and the like. The symbol "*" represents the bonding position.

Specific examples of the substituent (a) having a cyclic structure include a group having a dioxolane skeleton, such as a (4R,5R)-4,5-dimethyl-1,3-dioxolan-2-yl group, a (4S,5S)-4,5-dimethyl-1,3-dioxolan-2-yl group, a (4R,5R)-4,5-diethyl-1,3-dioxolan-2-yl group, and (4S,5S)-4,5-diethyl-1,3-dioxolan-2-yl group; a group having a dihydrooxazole skeleton, such as a (4R)-4-methyl-4,5-dihydrooxazol-2-yl group, (4S)-4-methyl-4,5-dihydrooxazol-2-yl group, a (5R)-5-methyl-4,5-dihydrooxazol-2-yl group, and a (5S)-5-methyl-4,5-dihydrooxazol-2-yl group; a group having a dihydrothiazole skeleton, such as a (4R)-4-methyl-4,5-dihydrothiazol-2-yl group, a (4S)-4-methyl-4,5-dihydrothiazol-2-yl group, a (5R)-5-methyl-4,5-dihydrothiazol-2-yl group, and a (5S)-5-methyl-4,5-dihydrothiazol-2-yl group; a group having a pyrrolidine skeleton, such as a (2R)-pyrrolidin-2-yl group, a (2S)-pyrrolidin-2-yl group, and a derivative thereof; and the like.

The single crystal of the porous compound used in connection with one embodiment of the invention includes the three-dimensional framework, and either or both of the pores and the voids that are defined by the three-dimensional framework, and are three-dimensionally arranged in an ordered manner.

Examples of the single crystal of the porous compound include a single crystal of a polynuclear metal complex.

Examples of the polynuclear metal complex include a polynuclear metal complex that includes a ligand having two or more coordinating moieties (hereinafter may be referred to as "multidentate ligand"), and a metal ion that serves as the center metal, and a polynuclear metal complex that includes a multidentate ligand, a metal ion that serves as the center metal, and a framework-forming aromatic compound.

The single crystal of the polynuclear metal complex used in connection with one embodiment of the invention may be prepared using a multidentate ligand that includes the substituent (a), or a framework-forming aromatic compound that includes the substituent (a). It is preferable that the single crystal of the porous compound be a single crystal of a polynuclear metal complex that includes a multidentate a metal ion that serves as the center metal, and a framework-forming aromatic compound that includes the substituent (a), since it is possible to efficiently prepare a single crystal of a polynuclear metal complex that includes various substituents (a) (as described later).

The multidentate ligand is not particularly limited as long as the multidentate ligand can form the three-dimensional framework. A known multidentate ligand may be used as the multidentate ligand.

The term "coordinating moiety" used herein refers to an atom or an atomic group included in the ligand that has an unshared electron pair that can form a coordinate bond. Examples of the coordinating moiety include a hetero atom such as a nitrogen atom, an oxygen atom, a sulfur atom, and a phosphorus atom; an atomic group such as a intro group, an amino group, a cyano group, and a carboxyl group; and the like. Among these, a nitrogen atom and an atomic group that includes a nitrogen atom are preferable.

It is preferable that the multidentate ligand include an aromatic ring since the planarity of the ligand is improved, and a strong three-dimensional framework is easily formed.

A single crystal of as polynuclear metal complex having relatively large pores and voids is normally obtained when a multidentate ligand is used in which the distance from the center of the ligand to the coordinating moiety is long, and a single crystal of a polynuclear metal complex having relatively small pores and voids is normally obtained when a multidentate ligand is used in which the distance from the center of the ligand to the coordinating moiety is short.

It is preferable to use a multidentate ligand haying two or more coordinating moieties, more preferably a multidentate ligand haying three coordinating moieties (hereinafter may be referred to as "tridentate ligand"), and still more preferably a tridentate ligand in which the unshared electron pairs (orbitals) of the three coordinating moieties are present in the same plane, and the three coordinating moieties are arranged radially with respect to the center of the tridentate ligand at an equal interval, since it is possible to easily obtain a single crystal having relatively large pores and voids.

The expression "present in the same plane" used herein includes a case where each unshared electron pair is present in the same plane, and a case where each unshared electron pair is present in a plane that is shifted to some extent (e.g., present in a plane that intersects a reference plane at an angle of 20° or less).

The expression "the three coordinating Moieties are arranged radially with respect to the center of the tridentate ligand at an equal interval" used herein means that the three coordinating moieties are arranged on lines that extend radially from the center of the ligand at an equal interval, at an almost equal distance from the center of the ligand.

Examples of the tridentate ligand include a ligand represented by the following formula (1).

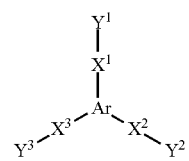

(1)

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety.

Ar in the formula (1) is a trivalent aromatic

The number of carbon atoms of the group represented by Ar is normally 3 to 22, preferably 3 to 13, and more preferably 3 to 6.

Examples of the group represented by Ar include a trivalent aromatic group having a monocyclic structure that consists of one 6-membered aromatic ring, and a trivalent aromatic group haying a fused ring structure in which three 6-membered aromatic rings are fused.

Examples of the trivalent aromatic group having a mono cyclic structure that consists of one 6-membered aromatic ring include the groups respectively represented by the following formulas (2a) to (2d). Examples of the trivalent aromatic group having a fused ring structure in which three 6-membered aromatic rings are fused, include the group represented by the following formula (2e). Note that the symbol "*" in the formulas (2a) to (2e) represents the positions at which $X^1$ to $X^3$ are bonded.

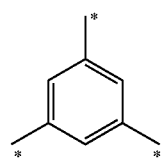

(2a)

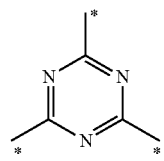

(2b)

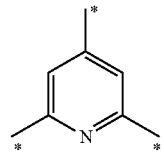

(2c)

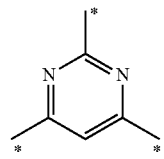

(2d)

-continued (2e)

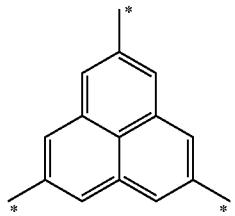

It is preferable that Ar be the aromatic group represented by the formula (2a) or (2b), and particularly preferably the aromatic group represented by the formula (2b).

The aromatic groups respectively represented by the formulas (2a) and (2c) to (2e) may be substituted with a substituent at an arbitrary position. Examples of the substituent include an alkyl group such as a methyl group, an ethyl group, an isopropyl group, an n-propyl group, and a t-butyl group; an alkoxy group such as a methoxy group, an ethoxy group, an n-propoxy group, and an n-butoxy group; a halogen atom such as a fluorine atom, a chlorine atom, and a bromine atom; the substituent (a); and the like.

$X^1$ to $X^3$ are independently a divalent organic group, or a single bond that directly bonds Ar and $Y^1$, $Y^2$, or $Y^3$.

The divalent organic group that may be represented by $X^1$ to $X^3$ is preferably a group that can form a π electron conjugated system together with Ar. When the divalent organic group that may be represented by $X^1$ to $X^3$ forms a π electron conjugated system, the planarity of the tridentate ligand represented by the formula (1) is improved, and a stronger three-dimensional framework structure is easily formed.

The number of carbon atoms of the divalent organic group is preferably 2 to 18, more preferably 2 to 12, and still more preferably 2. to 6.

Examples of the divalent organic group include a divalent unsaturated aliphatic group having 2 to 10 carbon atoms a divalent organic group having a monocyclic structure that consists of one 6-membered aromatic ring, a divalent organic group having a fused ring structure in which two to four 6-membered aromatic rings are fused, an amide group (—C(=O)—N—), an ester group (—C(=O)—O—), a combination of two or more divalent organic groups among these divalent organic groups, and the like.

Examples of the divalent unsaturated aliphatic group having 2 to 10 carbon atoms include a vinylene group, an acetylene group (ethynylene group), and the like.

Examples of the divalent organic group having a monocyclic structure that consists of one 6-membered aromatic ring, include a 1,4-phenylene group and the like.

Examples of the divalent organic group having a fused ring structure in which two to four 6-membered aromatic rings are fused, include a 1,4-naphthylene group, an anthracene-1,4-diyl group, and the like.

Examples of a combination of two or more divalent organic groups among these divalent organic groups include the groups shown below.

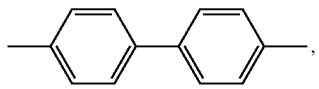

-continued

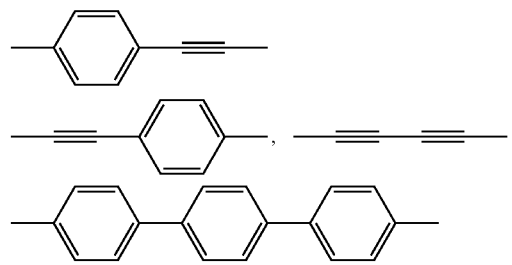

The groups shown below are preferable as the divalent organic group that may be represented by $X^1$ to $X^3$.

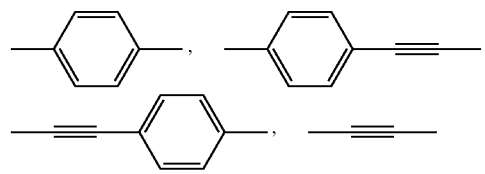

The aromatic ring included in the divalent organic group may include a hetero atom such as a nitrogen atom, an oxygen atom, or a sulfur atom.

The divalent organic group may be substituted with a substituent. Examples of the substituent include those mentioned above in connection with Ar.

$Y^1$ and $Y^3$ are independently a monovalent organic group having a coordinating moiety.

The organic group represented by $Y^1$ to $Y^3$ is preferably a group that can form a π electron conjugated system together with Ar and $X^1$ to $X^3$.

When the organic group represented by $Y^1$ to $Y^3$ forms a π electron conjugated system, the planarity of the tridentate ligand represented by the formula (1) is improved, and a strong three-dimensional framework structure is easily formed.

The number of carbon atoms of the organic group represented by $Y^1$ to $Y^3$ is preferably 5 to 11, and more preferably 5 to 7.

Examples of the organic group represented by $Y^1$ to $Y^3$ include the organic groups respectively represented by the following formulas (3a) to (3f). Note that the symbol "*" in the formulas (3a) to (3f) represents the position at which $X^1$, $X^2$, or $X^3$ is bonded.

(3a)

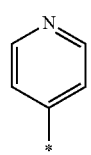

(3b)

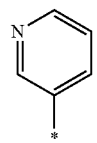

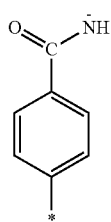 (3c)

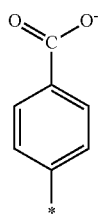 (3d)

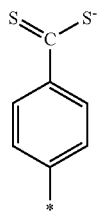 (3e)

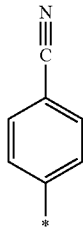 (3f)

The group represented by the formula (3a) is particularly preferable as $Y^1$ to $Y^3$.

The organic groups respectively represented by the formulas (3a) to (3f) may be substituted with a substituent at an arbitrary position. Examples of the substituent include those mentioned above in connection with Ar.

The size of the pores and the voids of the single crystal can be adjusted by appropriately selecting Ar, $X^1$ to $X^3$, and $Y^1$ to $Y^3$ included in the tridentate ligand represented by the formula (1). This makes it possible to efficiently obtain a single crystal that has pores and voids having a size sufficient to include the target chiral compound (A).

It is preferable that the tridentate ligand represented by the formula (1) have high planarity and high symmetry, and have a structure in which a π-conjugated system extends over the entire ligand, since a strong three-dimensional framework structure is easily formed. Examples of such a tridentate ligand include the ligands respectively represented by the following formulas (4a) to (4f), and the ligands respectively represented by the formulas (4a) to (4f) that are substituted with a substituent at an arbitrary position.

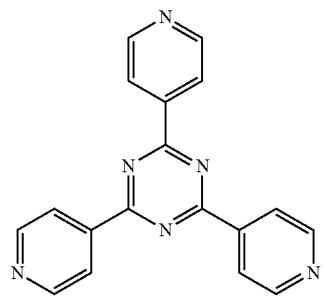 (4a)

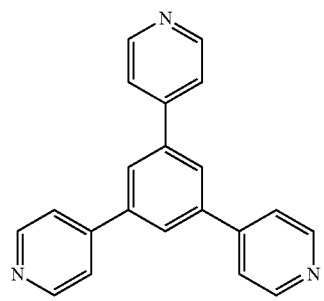 (4b)

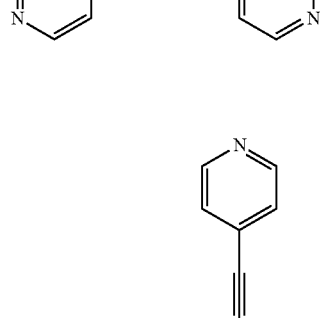 (4c)

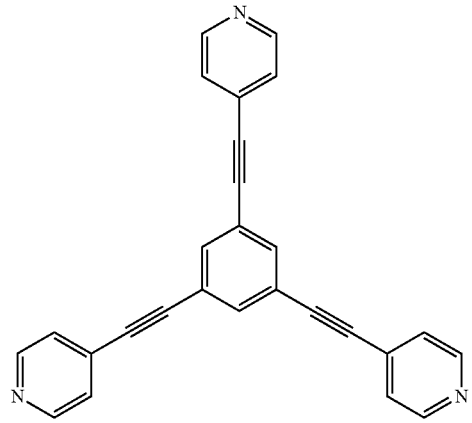 (4d)

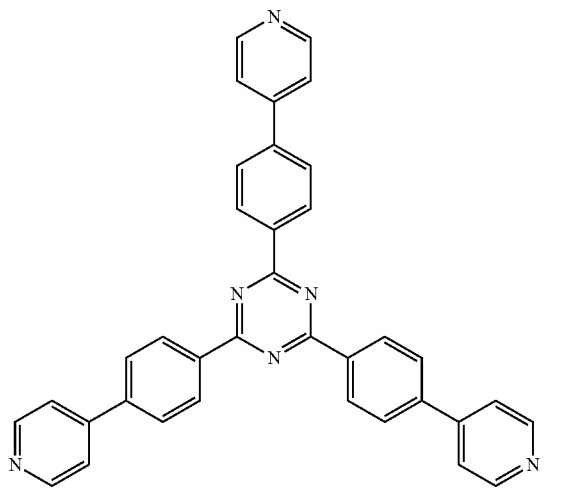

(4e)

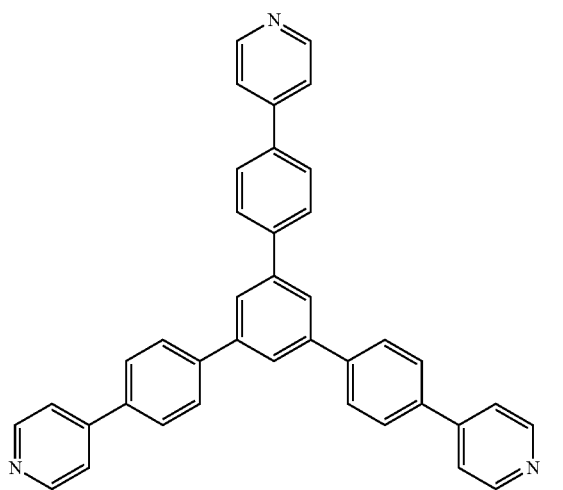

(4f)

Among these, 2,4,5-tris(4-pyridyl)-1,3,5-triazine (TPT) represented by the formula (4a) is particularly preferable as the tridentate ligand represented by the formula (1).

A commercially-available product may also be used as the multidentate ligand of the polynuclear metal complex. For example, Material Matters No. 7—Fundamentals of Porous Coordination Polymers (PCP)/Metal-Organic Frameworks (MOF) (September, 2012) published by Sigma-Aldrich lists pyrazine 14-diazabicyclo[2.2.2]octane 1,2-di(4-pyridyl)ethylene, 4,4'-bipyridyl 4,4'-biphenyldicarboxylic acid, benzene-1,3-dicarboxylic acid, pyrazine-2,3-dicarboxylic acid, pyrazine-3,5-dicarboxylic acid, and the like as a PCP/MOF ligand and a linker compound. These ligands may be used as the multidentate ligand of the polynuclear metal complex in a state in which the ligands are optionally substituted with a substituent at an arbitrary position.

The ligand that is substituted with a substituent at an arbitrary position may be a ligand that is substituted with the substituent (a) at an arbitrary position. The ligand that is substituted with the substituent (a) at an arbitrary position may be produced by introducing the substituent (a) into the unsubstituted ligand using a known method.

The metal ion that serves as the center metal of the polynuclear metal complex is not particularly limited as long as the metal ion forms a coordinate bond together with the multidentate ligand to form the three-dimensional framework. It is preferable to use an ion of a metal among the metals that respectively belong to Groups 8 to 12 in the periodic table, such as an iron ion, a cobalt ion, a nickel ion, a copper ion, a zinc ion, a silver ion, a palladium ion, a ruthenium ion, a rhodium ion, and a platinum ion, and more preferably an ion of a divalent metal among the metals that respectively belong to Groups 8 to 12 in the periodic table. It is particularly preferable to use a zinc(II) ion or a cobalt(II) ion since a single crystal having large pores and voids can be easily obtained.

A monodentate ligand may be coordinated to the center metal of the polynuclear metal complex in addition to the multidentate ligand. Examples of the monodentate ligand include a monovalent anion such as a chloride ion (Cl⁻), a bromide ion (Br⁻), an iodide ion (I⁻), and a thiocyanate ion (SCN⁻); an electrically neutral coordinating compound such as ammonia, a monoalkylamine, a dialkylamine, a trialkylamine, and ethylenediamine; and the like.

The polynuclear metal complex may include a reaction solvent a solvent used to synthesize the polynuclear metal complex), a replacement solvent (i.e., a solvent with which the reaction solvent is replaced (hereinafter the same)), and a framework-forming aromatic compound (described later).

The term "framework-forming aromatic compound" used herein refers to an aromatic compound that interacts with the molecular chain that forms the three-dimensional framework (excluding formation of a covalent bond and a coordinate bond) to form part of the three-dimensional framework.

When the polynuclear metal complex includes the framework-forming aromatic compound a stronger three-dimensional framework can be easily obtained, and the three-dimensional framework may be further stabilized even in a state in which the polynuclear metal complex includes the molecule of the chiral compound (A).

Examples of the framework-forming aromatic compound include a fused polycyclic aromatic compound. Examples of the fused polycyclic aromatic compound include the compounds respectively represented by the following formulas (5a) to (5i).

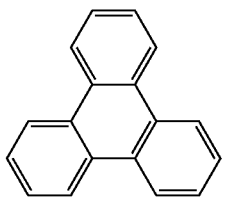

(5b)

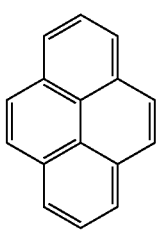

(5b)

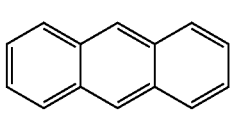

(5c)

-continued (5d)
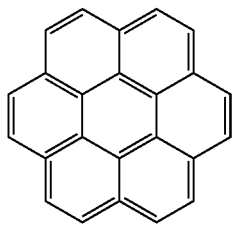

(5e)
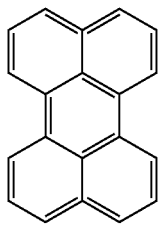

(5f)
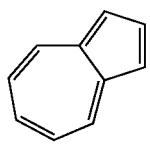

(5g)
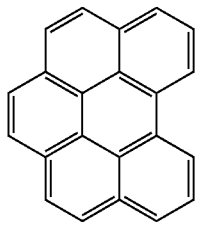

(5h)
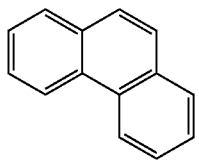

(5i)
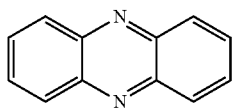

These fused polycyclic aromatic compounds may be substituted with a substituent at an arbitrary position. Examples of the substituent include those mentioned above in connection with Ar included in the multidentate ligand.

The substituent (a) is preferable as the substituent that substitutes the fused polycyclic aromatic compound.

It is normally efficient from the viewpoint of chemical syntheses to introduce the substituent (a) into the framework-forming aromatic compound instead of introducing the substituent (a) into the multidentate ligand. Therefore, it is possible to efficiently obtain single crystals of various polynuclear metal complexes by utilizing the framework-forming aromatic compound that includes the substituent (a).

The framework-forming aromatic compound that includes the substituent (a) may be produced by introducing the substituent (a) into the unsubstituted framework-forming aromatic compound using a known method.

Examples of the framework-forming aromatic compound that includes the substituent (a) include (4R,5R)-4,5-dimethyl-2-(triphenylen-2-yl)-1,3-dioxolane, (4S,5S)-4,5-dimethyl-2-(triphenylen-2-yl)-1,3-dioxolane, and the like.

Examples of the polynuclear metal complex include the compounds listed. below.

(1) Compound that includes only a ligand and a metal ion (polynuclear metal complex ($\alpha$))
(2) Compound that includes the polynuclear metal complex ($\alpha$) and the framework-forming aromatic compound (polynuclear metal complex ($\beta$))
(3) Compound that includes the polynuclear metal complex ($\alpha$) or the polynuclear metal complex ($\beta$), and a guest molecule (e.g., solvent molecule) included therein (polynuclear metal complex ($\delta$))

It is preferable that the polynuclear metal complex used in connection with one embodiment of the invention does not lose crystallinity, and have relatively large pores and voids, even after the molecule of the chiral compound (A) has been introduced into (incorporated in) the pores and the voids.

A polynuclear Metal complex having such properties can be easily obtained by utilizing the tridentate ligand represented by the formula (1).

Examples of the polynuclear metal complex that is obtained by utilizing the tridentate ligand represented by the formula (1) include polynuclear metal complexes respectively represented by the following formulas (6a) to (6c).

$$[(MX_2)_3(L)_2(solv)_a]_b \quad (6a)$$

$$[(MX_2)_3(L)_2(SA)_c(solv)_a]_b \quad (6b)$$

$$[(MX_2)_3(L)_4(solv)_a]_b \quad (6c)$$

wherein M is an on of a divalent metal among the metals that respectively belong to Groups 8 to 12 in the periodic table. X is a monovalent anionic monodentate ligand. L is the tridentate ligand represented by the formula (1), "solv" is a guest molecule (e.g., solvent molecule) used during synthesis, "SA" is the framework-forming aromatic compound, and a, b, and c are an arbitrary natural number. Note that at least one of L and SA includes the substituent (a).

The three-dimensional framework of the polynuclear metal complexes respectively represented by the formulas (6a) to (6c) can be estimated from the known three-dimensional framework of a polynuclear metal complex that is similar thereto.

Specifically, the molecular structure (into which a guest molecule (e.g., solvent molecule) is introduced) of a polynuclear metal complex that does not include the substituent (a), and includes TPT represented by the formula (4a) as L has been determined by X-ray single crystal structure analysis.

It is considered that the three-dimensional framework of the polynuclear metal complex used in connection with one embodiment of the invention is similar to the three-dimensional framework of a polynuclear metal complex that does not include the substituent (a) as long as the substituent (a) does not affect the three-dimensional framework of the polynuclear metal complex. The polynuclear metal complex that includes TPT represented by the formula (4a) as L, and does not include the substituent (a) (i.e., polynuclear metal complexes represented by the following formulas (7a) to (7d)) are described below.

$$[(ZnI_2)_3(TPT)_2(solv)_a]_b \quad (7a)$$

$$[(ZnBr_2)_3(TPT)_2(solv)_a]_b \quad (7b)$$

$$[(ZnI_2)_3(TPT)_2(SA)_c(solv)_a]_b \quad (7c)$$

$$[(Co(NCS)_2)_3(TPT)_4(solv)_a]_b \quad (7d)$$

wherein "solv", "SA", a, b, and c are the same as defined above. Note that L and SA do not include the substituent (a).

Note that the ligand and the solvent molecule may be hereinafter abbreviated as shown below.

PhNO$_2$: nitrobenzene
TPH: triphenylene
PER: perylene
MeOH: methanol
DCB: 1,2-dichlorobenzene (1) [(ZnI$_2$)$_3$(TPT)$_2$(solv)$_a$]$_b$(7a)

Examples of the polynuclear metal complex represented by the formula (7a) include [(ZnI$_2$)$_3$(TPT)$_2$(PhNO$_2$)$_{5.5}$]$_n$ (polynuclear metal complex 1) disclosed in JP-A-2008-214584 and J. Am. Chem. Soc. 2004, v. 126, pp. 16292-16293, and a polynuclear metal complex obtained by replacing all or some of the reaction solvent molecules included in the polynuclear metal complex 1 with a replacement solvent.

Figure 2:
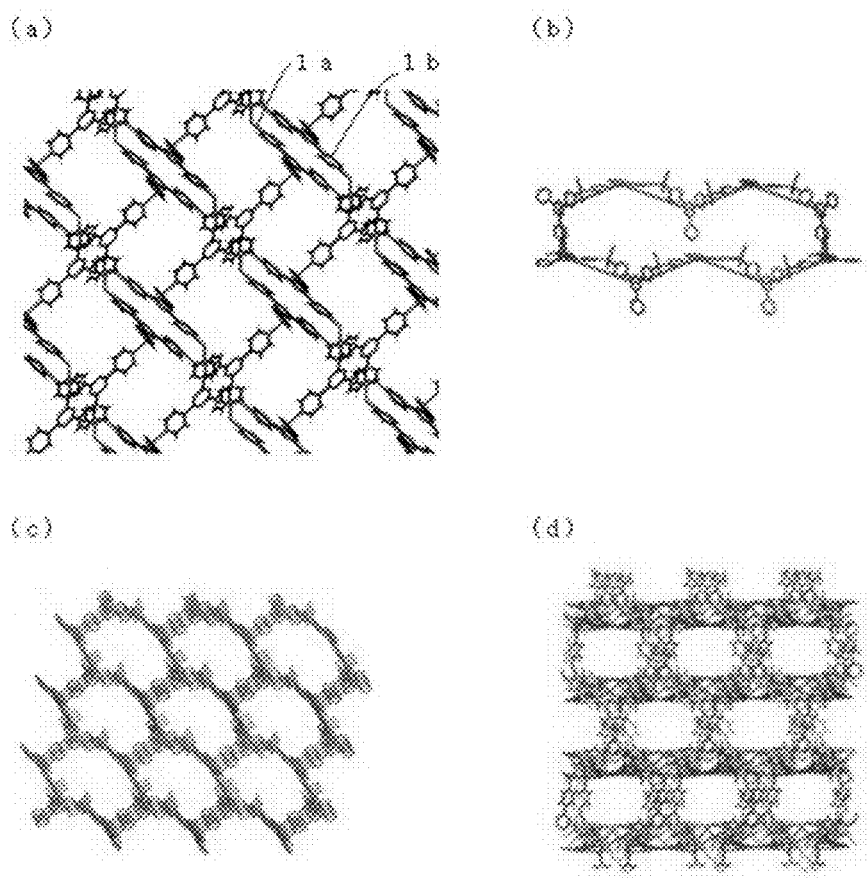
FIG. 2 is a view illustrating the three-dimensional framework of a polynuclear metal complex 1.

FIG. 2 (see (a) to (d)) illustrates the three-dimensional framework of the polynuclear metal complex 1.

The three-dimensional framework of the polynuclear metal complex 1 includes two molecular chains 1a and 1b. In the molecular chains 1a and 1b, the pyridyl groups of two TPT and two iodide ions are coordinated to each zinc(II) ion to form a tetra-coordinated tetrahedral structure. The structures including the zinc(II) ion are three-dimensionally connected through TPT to form each molecular chain (see (a) in FIG. 2).

The molecular chains 1a and 1b have a closed cyclic chain structure that consists of ten TPT molecules and ten Zn atoms as the shortest closed cyclic chain structure (see (b) in FIG. 2).

The molecular chains 1a and 1b are considered to be a helical hexagonal three-dimensional network structure in which the pitch along the (010) axis is 15 Å (see (c) in FIG. 2).

The molecular chains 1a and 1b do not share an identical zinc(II) ion, and are independent of each other. The molecular chains 1a and 1b penetrate each other in a complex nested form so as to share an identical space to form a single three-dimensional framework (assembly).

The single crystal of the polynuclear metal complex 1 having the three-dimensional framework has identical pores that are arranged in an ordered manner (see (d) in FIG. 2).

The void ratio of the single crystal of the polynuclear metal complex 1 is 50%.

The diameter of the pore inscribed circle of the single crystal of the polynuclear metal complex 1 is 5 to 8 Å.

(2) [(ZnBr$_2$)$_3$(TPT)$_2$(solv)$_a$]$_b$ (7b)

Examples of the polynuclear metal complex represented by the formula (7b) include [(ZnBr$_2$)$_3$(IPT)$_2$(PhNO$_2$)$_5$ (H$_2$O)]$_n$ (polynuclear metal complex 2) disclosed in JP-A-2008-214318, and a polynuclear metal complex obtained by replacing all or some of the reaction solvent molecules included in the polynuclear metal complex 2 with a replacement solvent.

The polynuclear metal complex 2 has the same three-dimensional framework as that of the polynuclear metal complex 1, except that (ZnI$_2$) is replaced by (ZnBr$_2$).

The pore shape, the pore size, and the void ratio of the single crystal of the polynuclear metal complex 2 are almost the same as those of the single crystal of the polynuclear metal complex 1.

(3) [(ZnI$_2$)$_3$(TPT)$_2$(SA)(solv)$_a$)]$_b$ (7c)

Examples of the polynuclear metal complex represented by the formula (7c) include [(ZnI)$_3$(TPT)$_2$(TPH)(PhNO$_2$)$_{3.9}$ (MeOH)$_{1.8}$]$_n$ (polynuclear metal complex 3) and [(ZuI$_2$)$_3$ (TPT)$_2$(PER)(PhNO$_2$)$_4$]$_n$ (polynuclear metal complex 4) disclosed in JP-A-2006-188560, and a polynuclear metal complex obtained by replacing all or some of the reaction solvent molecules included in the polynuclear metal complex 3 or 4 with a replacement solvent.

Figure 3:
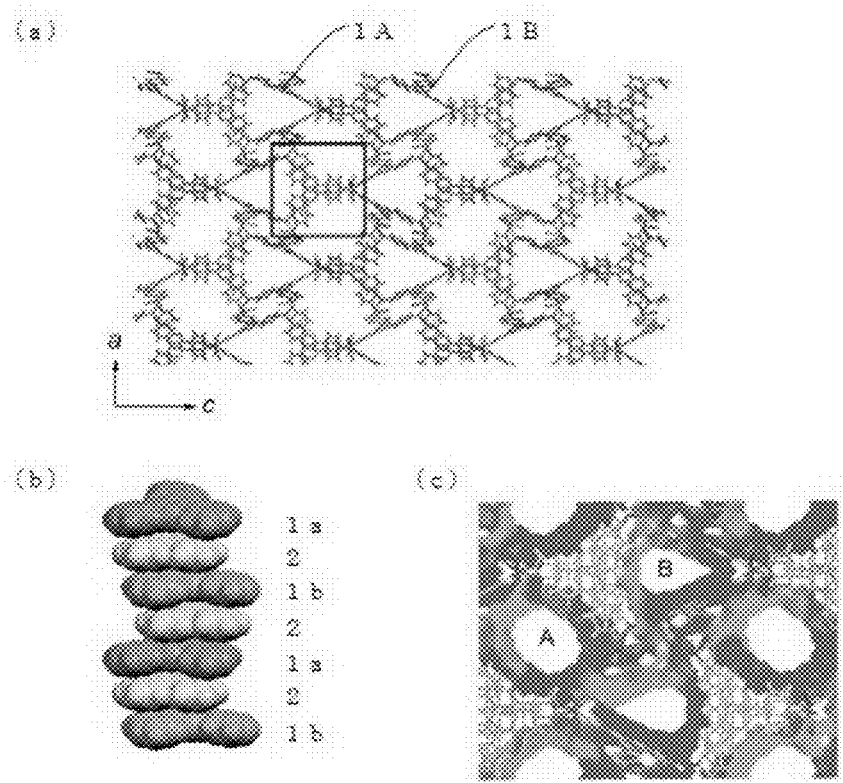
FIG. 3 is a view illustrating the three-dimensional network structure of a polynuclear metal complex 3.

FIG. 3 (see (a) to (c)) illustrates the three-dimensional framework of the polynuclear metal complex 3.

The three-dimensional framework of the polynuclear metal complex 3 is formed by two molecular chains 1A and 1B, and a triphenylene molecule (i.e., framework-forming aromatic compound).

In the molecular chains 1A and 1B, two iodide ions and the pyridyl groups of two TPT are coordinated to each zinc(II) ion to form a tetra-coordinated tetrahedral structure. The structures including the zinc(II) ion are three-dimensionally connected through TPT to form the molecular chain.

The molecular chains 1A and 1B do not share an identical zinc(II) ion, and are independent of each other. The molecular chains 1A and 1B penetrate each other in a complex nested form so as to share an identical space to form a single three-dimensional framework (assembly).

The triphenylene molecule (2) included in the polynuclear metal complex 3 is firmly intercalated between the π plane of tris(4-pyridyl)triazine (TPT (1a)) of the molecular chain 1A and the π plane of tris(4-pyridyl)triazine (TPT (1b)) of the molecular chain 1B (see (b) in FIG. 3). The triphenylene molecule is stabilized by the π-π interaction between TPT (1a) and TPT (1b), and serves as part of the three-dimensional framework of the polynuclear metal complex 3. In FIG. 3, (b) is a side view illustrating the area enclosed in (a).

The single crystal of the polynuclear metal complex 3 has two types of pores (pores A and B) that are arranged in an ordered manner (see (c) in FIG. 3). The pores A and B are formed in an ordered manner in a laminate structure in which TPT and TPH are alternately stacked.

The pore A has an approximately cylindrical shape, and is almost completely surrounded by the hydrogen atoms present at the side edge of the π planes of a number of TPT and TPH that are stacked.

The pore B is approximately in the shape of a triangular prism. Two sides among the three sides of the triangular prism are surrounded by the π planes of TPT, and the remaining side is surrounded by the hydrogen atoms present at the side edge of the π planes of a number of TPT and TPH that are stacked.

The pores A and B have an elongated shape that meanders to some extent.

The void ratio of the single crystal of the polynuclear metal complex 3 is 28%.

The diameter of the circle inscribed to the pore A of the single crystal of the polynuclear metal complex 3 is 5 to 8 Å.

The diameter of the circle inscribed to the pore B of the single crystal of the polynuclear metal complex 3 is 5 to 8 Å.

The polynuclear metal complex 4 has the same framework structure as that of the polynuclear metal complex 3, except that the perylene molecule is intercalated between two TPT instead of a triphenylene molecule.

The pore shape, the pore size, and the void ratio of the single crystal of the polynuclear metal complex 4 are almost the same as those of the single crystal of the polynuclear metal complex 3.

(4) [(Co(NCS)$_2$)$_3$(TPT)$_4$(solv)$_a$]$_b$ (7d)

Examples of the polynuclear metal complex represented by the formula (7d) include [(Co(NCS)$_2$)$_3$(TPT)$_4$(DCB)$_{25}$(MeOH)$_5$]$_n$ (polynuclear metal complex 5) disclosed in WO2011/1052260, and as polynuclear metal complex obtained by replacing all or some of the reaction solvent molecules included in the polynuclear metal complex 5 with a replacement solvent.

Figure 4:
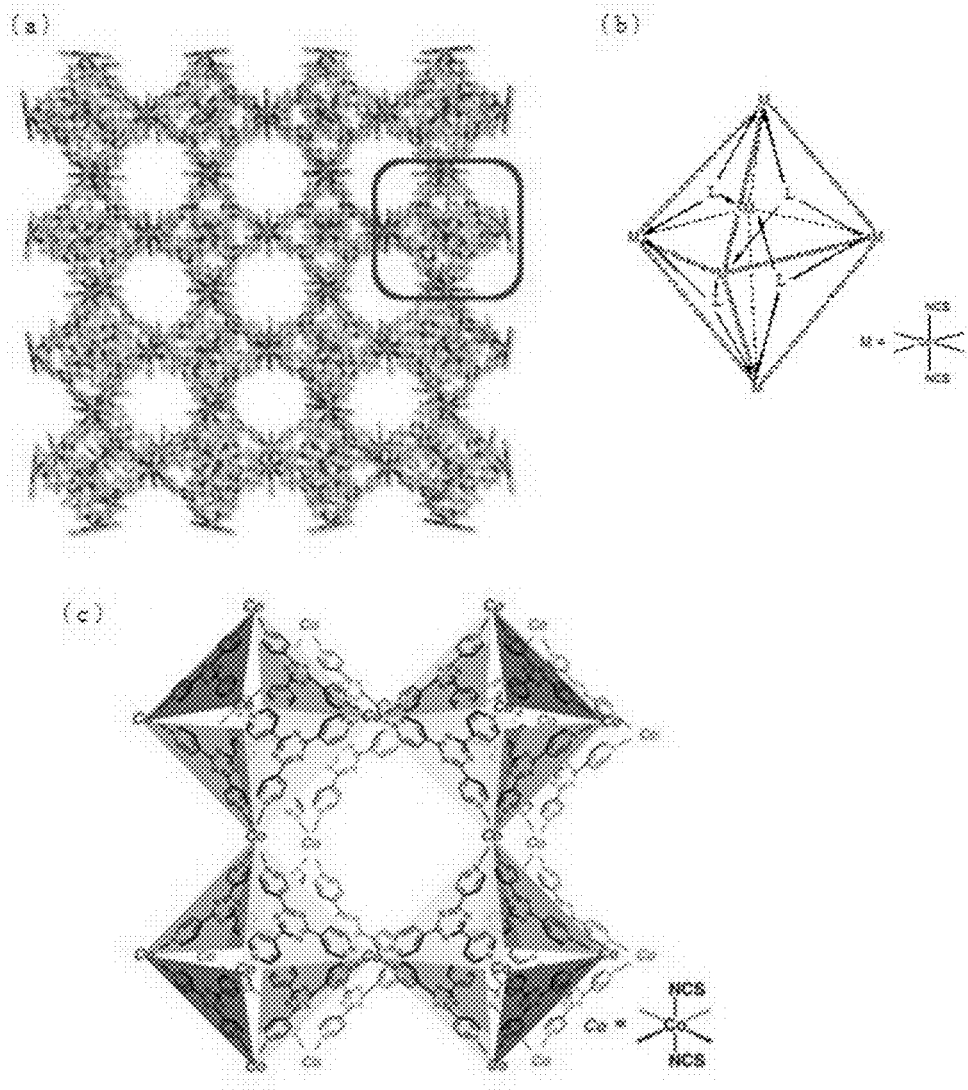
FIG. 4 is a view illustrating the three-dimensional network structure of a polynuclear metal complex 5.

FIG. 4 (see (a)) illustrates the three-dimensional framework of the polynuclear metal complex 5.

The polynuclear metal complex 5 has a (Co$_6$(TPT)$_4$) structure that includes six cobalt ions and four TPT as a structural unit. The structural unit has an octahedral shape in which a cobalt ion is situated at each vertex of the octahedron (see (b) in FIG. 4). The pyridyl groups of four TPT and two thiocyanate ions are coordinated to each cobalt(II) ion to form a hexa-coordinated octahedral structure. In FIG. 4, (b) is an enlarged view illustrating the area enclosed in (a).

The (Co$_6$(TPT)$_4$) structures are three-dimensionally connected so as to share the cobalt ion situated at each vertex of each (Co$_6$(TPT)$_4$) structure to form pores between the (Co$_6$(TPT)$_4$) structures (see (c) in FIG. 4).

The structural unit has a void therein.

The void ratio of the single crystal of the polynuclear metal complex 5 is 78%. This value is calculated using the total volume of the pores and the voids.

The diameter of the pore inscribed circle of the single crystal of the polynuclear metal complex 5 is 10 to 18 Å.

The method for preparing a crystal structure analysis sample according to one embodiment of the invention may utilize a single crystal of a polynuclear metal complex that has the same three-dimensional framework structure as that of a polynuclear metal complex among the polynuclear metal complexes respectively represented by the formulas (7a) to (7d), and includes the substituent (a) (that is obtained by utilizing a multidentate ligand or a framework-forming aromatic compound that includes the substituent (a)) as the single crystal of the porous compound instead of the multidentate ligand (TPT) or the framework-forming aromatic compound included in a polynuclear metal complex among the polynuclear metal complexes respectively represented by the formulas (7a) to (7d).

A known polynuclear metal complex referred to as a porous coordination polymer (PCP) or a metal-organic framework (MOF) may be used as the polynuclear metal complex instead of a polynuclear metal complex that includes the tridentate ligand represented by the formula (1). For example, Material Matters No. 7 -Fundamentals of Porous Coordination Polymers (PCP)/Metal-Organic Frameworks (MOF) (September, 2012) published by Sigma-Aldrich lists polynuclear metal complexes such as [Cu$_2$(bzdc)$_2$(pyz)]$_n$ (wherein bzde is 2,3-pyrazinedicarboxylic acid, pyz is pyrazine, and n is an arbitrary number), [Zn$_2$(14bdc)$_2$(dabco)]$_n$ (wherein 14bdc is 1,4-benzenedicarboxylic acid, dabco is 1,4-diazabicyclo[1.2.2]octane, and it is an arbitrary number), [Cu(dtc)$_2$]$_n$ (wherein H$_3$dhbpc is 4,4'-dihydroxybiphenyl-3-carboxylic acid, bpy is 4,4'-bipyridyl, and n is an arbitrary number), and [Cr(btc)$_2$]$_n$ (wherein H$_3$btc is 1,3,5-benzenetricarboxylic acid, and n is an arbitrary number).

The method for preparing a crystal structure analysis sample according to one embodiment of the invention may utilize a single crystal of a polynuclear metal complex obtained using a multidentate ligand that includes the substituent (a) instead of the multidentate ligand included in a polynuclear metal complex among the above polnuclear metal complexes as the single crystal of the porous compound.

When implementing the method for preparing a crystal structure analysis sample according to one embodiment of the invention, it is preferable that the single crystal of the polynuclear metal complex include the tridentate ligand represented by the formula (1), a metal ion that serves as the center metal, and the framework-forming compound that includes a chiral substituent of which the absolute configuration is known, and the chiral substituent of which the absolute configuration is known be a group among the groups respectively represented by the following formulas.

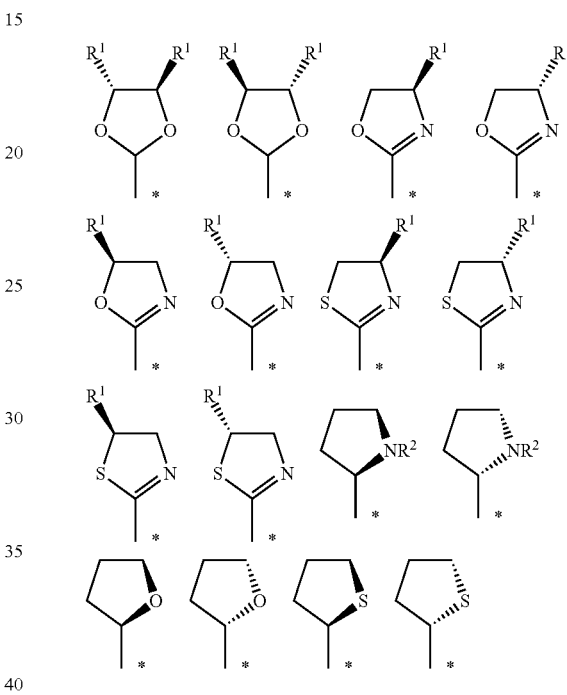

wherein R$^1$ is an alkyl group having 1 to 5 carbon atoms, and R$^2$ is a hydrogen atom or an alkyl group having 1 to 5 carbon atoms. Examples of the alkyl group having 1 to 5 carbon atoms that (may be) represented by R$^1$ and R$^2$ include a methyl group, an ethyl group, and the like. The symbol "*" represents the bonding position.

The details of the tridentate ligand represented by the formula (1), the metal ion that serves as the center metal, and the framework-forming, compound that includes the chiral substituent of which the absolute configuration is blown, are the same as described above.

The polynuclear metal complex may be synthesized using an arbitrary method. The polynuclear metal complex may be synthesized using a known method.

For example, Material Matters No. 7—Fundamentals of Porous Coordination Polymers (PCP)/Metal-Organic Frameworks (MOF) (September, 2012) published by Sigma-Aldrich describes a solution method that mixes a solution that includes a multidentate ligand and the like with a solution that includes a metal ion and the like; a hydrothermal method that charges a pressure-resistant vessel with a solvent, a multidentate ligand, a metal ion, and the like, seals the pressure-resistant vessel, and heats the mixture to a temperature equal to or higher than the boiling point of the solvent to effect a hydrothermal reaction; a microwave method that charges a vessel with a solvent, a multidentate ligand, a metal ion, and the like, and applies microwaves to the mixture; an ultrasonic method that charges a vessel with a solvent, a multidentate ligand, a metal ion, and the like, and applies ultrasonic waves to the mixture; a solid-state synthesis method that mechanically mixes a multidentate ligand, a metal ion, and the like without using a solvent; and the like. A single crystal of the polynuclear metal complex can be obtained using these methods.

It is preferable to use the solution method since the solution method does not require special equipment and the like.

For example, a solvent solution prepared by dissolving a metal ion-containing compound in a second solvent is added to a solvent solution prepared by dissolving a multidentate ligand in a first solvent, and the mixture is allowed to stand at 0 to 70° C. for several hours to several days.

The metal ion-containing compound is not particularly limited. Examples of the metal ion-containing compound include a compound represented by $MX_n$. Note. that M is as metal ion, X is a counter ion, and n is the valence of M.

Specific examples of X include $F^-$, $Cl^-$, $Br^-$, $I^-$, $SCN^-$, $NO_3^-$, $ClO_4^-$, $BF_4^-$, $SbF_4^-$, $PF_6^-$, $AsF_6^-$, $CH_3CO_2^-$, and the like.

Examples of the reaction solvent (first solvent and second solvent) include an aromatic hydrocarbon such as benzene, toluene, xylene, chlorobenzene, 1,2-dichlorobenzene, and nitrobenzene; an aliphatic hydrocarbon such as n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide (DMSO); an amide such as N,N -dimethylformamide and N-methylpyrrolidone; an ether such as diethyl ether, tetrahydrofuran, 1,2-dimetboxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

When it is desired to obtain a relatively large single crystal of the polynuclear metal complex, it is preferable that the first solvent and the second solvent be immiscible with each other (i.e., separated into two layers). For example, nitrobenzene, dichlorobenzene, a mixed solvent including nitrobenzene and methanol, or a mixed solvent including dichlorobenzene and methanol may be used as the first solvent, and methanol may be used as the second solvent.

A polynuclear metal complex having the same three-dimensional framework structure as that of a polynuclear metal complex among the polynuclear metal complexes 1 to 5 can be synthesized using the methods described in the above literature.

(iv) Step that Brings Single Crystal of Porous Compound into Contact with Solvent Solution that Includes Chiral Compound (A)

The single crystal of the porous compound may be brought into contact with the solvent solution that includes the chiral compound (A) using an arbitrary method. For example, the single crystal of the porous compound may be brought into contact with the solvent solution that includes the chiral compound (A) using a method that immerses the single crystal of the porous compound in the solvent solution that includes the chiral compound (A), or a method that charges a capillary with the single crystal of the porous compound, and passes the solvent solution that includes the chiral compound (A) through the capillary.

It is preferable to use the method that immerses the single crystal of the porous compound in the solvent solution that includes the chiral compound (A), since it is possible to efficiently bring the single crystal of the porous compound into contact with the solvent solution that includes the chiral compound (A).

It is preferable to immerse the single crystal of the porous compound in the solvent solution that includes the chiral compound (A) so that a value A calculated by the following expression (I) is 100 or less, more preferably 0.1 to 30, and still more preferably 1 to 5.

$$A = \frac{X}{Y} \quad (I)$$

where, X is the mass of the chiral compound (A) included in the solvent solution, and Y is the mass of a substance having a specific gravity of 1 that is required to fill all of the pores and the voids of the single crystal of the porous compound with the substance having a specific gravity of 1.

When the value A is 0.1 or more, the molecule of the chiral compound (A) is sufficiently introduced into the pores and the voids of the single crystal of the porous compound, and a high-quality crystal structure analysis sample is easily obtained. The target crystal structure analysis sample can be obtained even when the value A is large. However, a further improvement in effect may not be achieved, and the chiral compound (A) may be wasted.

The number of single crystals to be immersed in the solvent solution that includes the chiral compound (A) is not particularly limited. When the amount of the chiral compound (A) is very small, the target crystal structure analysis sample can be obtained by immersing one single crystal in the solvent solution that includes the chiral compound (A). When the amount of the chiral compound (A) is large, two or more single crystals of an identical porous compound may be immersed in the solvent solution that includes the chiral compound (A), or single crystals of different porous compounds may be immersed in the solvent solution that includes the chiral compound (A) at the same time.

After immersing the single crystal of the porous compound in the solvent solution that includes the chiral compound (A), the solvent may be volatilized under mild conditions to concentrate the solvent solution. This makes it possible to efficiently introduce the molecule of the chiral compound (A) into the pores and the voids of the single crystal of the porous compound.

The immersion conditions (concentration conditions) are not particularly limited. The temperature of the solvent solution is preferably 0 to 180° C., more preferably 0 to 80° C., and still more preferably 20 to 60° C.

The immersion time (concentration time) is normally 6 hours or more, preferably 12 to 168 hours, and more preferably 24 to 78 hours.

The volatilization rate of the solvent is preferably 0.1 to 1,000 µL/24 hours, more preferably 1 to 100 µL/24 hours, and still more preferably 5 to 50 µL/24 hours.

If the volatilization rate of the solvent is too high, it may be difficult to obtain a high-quality crystal structure analysis sample. If the volatilization rate of the solvent is too low the work efficiency may deteriorate.

The temperature employed when volatilizing the solvent is determined taking account of the boiling point of the organic solvent, but is normally 0 to 120° C. and preferably 15 to 60° C.

The operation that volatilizes the solvent after immersing the single crystal of the porous compound in the solvent solution that includes the chiral compound (A) to concentrate the solvent solution may be performed under normal pressure, or may be performed under reduced pressure, or may be performed under high pressure.

The pressure employed when performing the operation that volatilizes the solvent to concentrate the solvent solution is normally 1 to $1\times10^6$ Pa, and preferably $1\times10$ to $1\times10^6$ Pa.

The volatilization rate of the solvent can be appropriately adjusted by thus adjusting the temperature and the pressure employed when performing the operation that concentrates the solvent solution.

The molecule of the solvent used to prepare the solvent solution may be introduced into the pores and the voids of the single crystal of the porous compound before bringing the single crystal of the porous compound into contact with the solvent solution that includes the chiral compound (A). In this case, since the solvent molecules and the like used to synthesize the porous compound are removed from the pores and the voids of the single crystal of the porous compound, and the solvent that can be easily replaced by the molecule of the chiral compound (A) is introduced into the pores and the voids of the single crystal of the porous compound, it is possible to efficiently prepare high-quality crystal structure analysis sample.

The molecule of the solvent used to prepare the solvent solution may be introduced into the pores and the voids of the single crystal of the porous compound using a method that immerses the single crystal in the solvent that is used to prepare the solvent solution that includes the chiral compound (A).

The immersion conditions are not particularly limited. The temperature of the solvent is normally 0 to 70° C., preferably 10 to 60° C., and more preferably 20 to 50° C., and the immersion time is normally 6 hours or more, preferably 12 to 168 hours, and more preferably 24 to 78 hours.

(v) Crystal Structure Analysis Sample

A crystal structure analysis sample obtained using the method for preparing a crystal structure analysis sample according to one embodiment of the invention has a configuration in which the molecules of the chiral compound (A) are arranged in the pores and the voids of the single crystal of the porous compound in an ordered manner.

The expression "the molecules of the chiral compound (A) are arranged in an ordered manner" means that the molecules of the chiral compound (A) are included in the pores and the voids of the single crystal of the porous compound in an ordered manner to such an extent that the structure of the chiral compound (A) can be determined by crystal structure analysis.

It is preferable that the crystal structure analysis sample obtained using the method for preparing a crystal structure analysis sample according to one embodiment of the invention be designed so that the molecular structure can be determined at a resolution of at least 1.5 Å when applying MoKα radiation (wavelength: 0.71 Å) generated at a tube voltage of 24 kV and a tube current of 50 mA to the crystal structure analysis sample, and detecting diffracted X-rays using a CCD detector.

In the crystal structure analysis sample obtained using the method for preparing a crystal structure analysis sample according to one embodiment of the invention, the molecule of the chiral compound (A) need not necessarily be included in all of the pores and the voids of the single crystal of the porous compound as long as the structure of the chiral compound (A) can be determined. For example, the solvent used to prepare the solvent solution that includes the chiral compound (A) may be included in some of the pores and the voids of the single crystal of the porous compound.

It is preferable that the occupancy ratio of the molecules of the chiral compound (A) in the crystal structure analysis sample obtained using the method for preparing a crystal structure analysis sample according to one embodiment of the invention be 10% or more.

The term "occupancy ratio" used herein in connection with the molecules of the chiral compound (A) refers to a value obtained by crystal structure analysis, and represents the amount of guest molecules actually present in the single crystal with respect to the amount (=100%) of guest molecules the molecules of the chiral compound (A)) in an ideal inclusion state.

The crystal structure analysis sample obtained using the method for preparing a crystal structure analysis sample according to one embodiment of the invention makes it possible to determine the structure of the chiral compound (A) that is available in only a trace amount, or is liquid at room temperature (20° C.), by crystal structure analysis.

It is considered that the desired crystal structure analysis sample can be obtained using the method for preparing a crystal structure analysis sample according to one embodiment of the invention since the single crystal of the porous compound used in connection with one embodiment of the invention functions as a field that adjusts the orientation of the molecules of the chiral compound (A) as described below.

It is considered that many substances have a self-assembly capability protein molecules form a single crystal), and it is likely that a single crystal can be obtained by effecting crystallization under optimum crystallization conditions.

However, it is difficult to obtain a single crystal from a number of substances since it is difficult to determine optimum crystallization conditions, or it is difficult to provide a sample in an amount sufficient to examine the crystallization conditions.

It is considered that the single crystal of the porous compound used in connection with one embodiment of the invention provides such substances with "a field" that promotes crystallization.

Specifically, when either or both of pores and voids that are three-dimensionally arranged in an ordered manner are formed in the single crystal in advance, it is considered that the molecules of the chiral compound (A) are affected by the regularity of "the field" when introduced into either or both of the pores and the voids of the single crystal, so that the self-assembly capability of the molecules of the chiral compound (A) is improved, and a crystal structure analysis sample in which the molecules of the chiral compound (A) have a uniform orientation can be obtained.

Therefore, it is considered that a single crystal that includes a three-dimensional framework, and either or both of pores and voids that are defined by the three-dimensional framework, and are three-dimensionally arranged in an ordered manner, has the effect of causing the molecules of the chiral compound (A) to have a uniform orientation at least to some extent.

It is possible to efficiently determine the absolute configuration of the chiral compound (A) by performing crystal structure analysis using the resulting crystal structure analysis sample (as described below).

2) Method for Determining Absolute Configuration of Chiral Compound

A method for determining the absolute configuration of a chiral compound according to one embodiment of the invention includes determining the absolute configuration of a chiral compound by crystal structure analysis using a crystal structure analysis sample obtained using the method for preparing a crystal structure analysis sample according to one embodiment of the invention.

When analyzing the molecular structure of a chiral compound by X-ray crystal structure analysis, there may be a case where it is possible to determine the relative positional relationship between the atoms, the distance between the atoms, and the like from the analysis results, but it is impossible to accurately determine the absolute configuration ((S) or (R)) of the chiral compound.

The method for determining the absolute configuration of a chiral compound according to one embodiment of the invention can easily determine the absolute configuration of the target chiral compound based on the relative positional relationship with the chiral group of which the absolute configuration is known (i.e., using the chiral group as a marker) by introducing the chiral group (of which the absolute configuration is known) into the voids of the porous compound, introducing the chiral compound for which the absolute configuration is to be determined into the voids of the porous compound to obtain a single crystal of an inclusion complex, and performing crystal structure analysis using the single crystal. The method for determining the absolute configuration of a chiral compound according to one embodiment of the invention can easily determine the absolute configuration of the target chiral compound without using a heavy atom method that utilizes the anomalous dispersion effect due to a heavy atom, or a method that introduces a chiral auxiliary (of which the absolute configuration is known) into the molecule of a chiral compound through an ionic bond or a covalent bond, and determines the absolute configuration of the chiral compound from the relative positional relationship with the chiral auxiliary.

The method for determining the absolute configuration of a chiral compound according to one embodiment of the invention may utilize X-ray diffraction or neutron diffraction.

When determining the absolute configuration of the chiral compound (A) using the method for determining the absolute configuration of a chiral compound according to one embodiment of the invention, crystal structure analysis is performed in the same manner as a known method, except that a crystal structure analysis sample obtained using the method for preparing a crystal structure analysis sample according to one embodiment of the invention is mounted instead of a known single crystal.

In this case, the absolute configuration of the chiral compound (A) can be determined in the same manner as in the case of using a method that determines the absolute configuration using a chiral auxiliary (i.e., a method that introduces a chiral auxiliary (of which the absolute configuration is known) into the molecule of a chiral compound, and determines the absolute configuration of the chiral compound from the relative positional relationship with the chiral auxiliary).

The method for determining the absolute configuration of a chiral compound according to one embodiment of the invention can efficiently determine the absolute configuration of a chiral compound.

In particular, the method for determining the absolute configuration of a chiral compound according to one embodiment of the invention can be used even when the amount of chiral compound is very small, and can efficiently determine the absolute configuration of a trace amount of impurities (included in a drug, an agricultural chemical, or a raw material) or various metabolites.

EXAMPLES

The invention is further described below by way of examples and comparative examples. Note that the invention is not limited to the following examples.

Equipment (1) Single Crystal X-ray Structure Analysis

Single crystal X-ray structure analysis was performed using an APEX II/CCD diffractometer (manufactured by Bruker, radiation source: Mo—Kα radiation (wavelength: 0.71 Å), output: 50 mA, 24 kV).

(2) Elemental Analysis

Elemental analysis was performed using an analyzer "MT-6" (manufactured by YANACO).

Production Example 1

Preparation of Ligand Solution 6.3 mg of 2,4,6-tris(4-pyridyl)-1,3,5-triazine (TPT) and 32.8 mg of (4R,5R)-4,5-dimethyl-2-(triphenylen-2-yl)-1,3-dioxolane were dissolved in a nitrobenzene/methanol (4 mL/1 mL) mixture to obtain a ligand solution.

Production Example 2

Preparation of Metal Ion-containing Solution 9.6 mg of $ZnI_2$ was dissolved in 0.5 mL of methanol to obtain a metal ion-containing solution.

Production Example 3

Synthesis of Single Crystal of Porous Compound

The ligand solution obtained in Production Example 1 was put in a test tube (diameter: 15 min. height: 12 cm), and 0.5 mL of methanol was slowly added to the ligand solution. The Metal ion-containing solution obtained in Production Example 2 was slowly added to the methanol layer so as to form an additional layer.

The solutions were allowed to stand at 15 to 25° C. for 7 days to obtain crystals of a polynuclear metal complex A. After removing the supernatant liquid by decantation cyclohexane was poured into the mixture. This operation was repeated to replace the solvent with cyclohexane. The crystals were allowed to stand at room temperature for 5 days in a state in which the crystals were immersed in 10 mL of cyclohexane to saturate the pores of the crystals with cyclohexane.

A single crystal was then selected, and subjected to X-ray crystal structure analysis.

Figure 5:
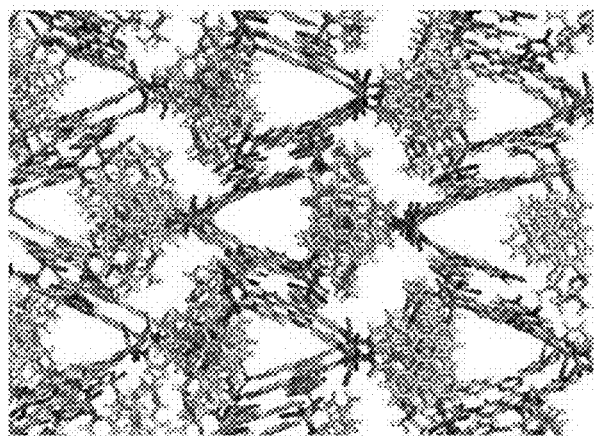
FIG. 5 is a view illustrating a polynuclear metal complex used in Examples 1 to 4 and 9.

Table 1 shows the crystallographic data, and FIG. 5 illustrates the crystal structure. Note that the unit for R1 in Table 1 is % (hereinafter the same).

TABLE 1

| Crystal system | Orthorhombic |
| --- | --- |
| Space group | $P2_12_12_1$ |
| a (Å) | 13.925 (2) |
| b (Å) | 28.776 (5) |
| c (Å) | 44.580 (8) |
| α (°) | 90 |
| β (°) | 90 |
| γ (°) | 90 |
| Z | 4 |
| R1 | 7.63 |

Example 1

A micro-vial was charged with the single crystal of the polynuclear metal complex A obtained in Production Example 3. After the addition of 50 µL of (R)-4-chloromethyl-2,2-dimethyl-1,3-dioxolane having the structure represented by the following formula, the mixture was allowed to stand at 15 to 25° C. for 2 days to obtain a crystal structure analysis sample. The crystal structure analysis sample was subjected to X-ray crystal structure analysis.

Figure 6:
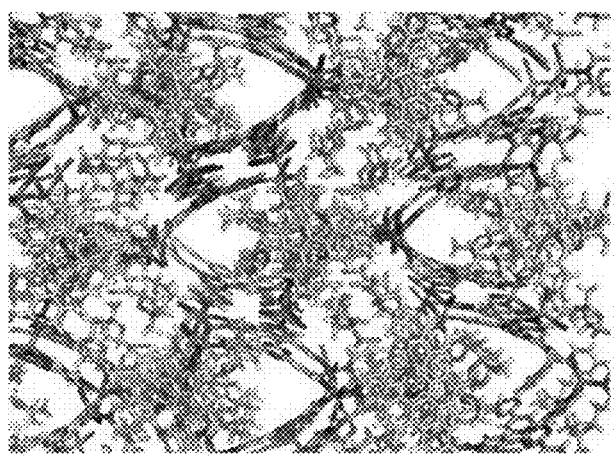
FIG. 6 is a view illustrating a polynuclear metal complex including (R)-4-chloromethyl-2,2-dimethyl-1,3-dioxolane obtained in Example 1.

Table 2 shows the crystallographic data, and FIG. 6 illustrates the crystal structure.

Atoms corresponding to the host framework (three-dimensional framework) and the guest molecule (4-chloromethyl-2,2-dimethyl-1,3-dioxolane) were assigned to the electron density observed during the crystal structure analysis. The absolute configuration of the dioxolane moiety of the host framework and the absolute configuration of the guest molecule were then compared using the analytical data. It was thus found that the crystal structure analysis sample had a stereochemical structure. including (4R,5R)-4,5-dimethyl-2-(triphenylen-2-yl)-1,3-dioxolane and (R)-4-chloromethyl-2,2-dimethyl-1,3-dioxolane.

Since the absolute configuration of (4R,5R)-4,5-dimethyl-2-(triphenylen-2-yl)-1,3-dioxolane (host framework) determined using the analytical data coincides with the absolute configuration of the compound actually used, it is considered that the absolute configuration of (R)-4-chloromethyl-2,2-dimethyl-1,3-dioxolane is correct.

Note that it may be determined from the reflection data that the crystal structure analysis sample had a stereochemical structure including (4S,5S)-4,5-dimethyl-2-(triphenylen-2-yl)-1,3-dioxolane and (S)-4-chloromethyl-2,2-dimethyl-1,3-dioxolane. In this case, however, since the absolute configuration of the chiral reference material (4,5-dimethyl-2-(triphenylen-2-yl)-1,3-dioxolane) of which the absolute configuration is known, is reversed, the absolute configuration "(S)-4-chloromethyl-2,2-dimethyl-1,3-dioxolane" is incorrect.

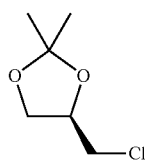

TABLE 2

| Crystal system | Orthorhombic |
| --- | --- |
| Space group | $P2_12_12_1$ |
| a (Å) | 13.925 (2) |
| b (Å) | 28.776 (5) |
| c (Å) | 44.580 (8) |
| α (°) | 90 |
| β (°) | 90 |
| γ (°) | 90 |
| Z | 4 |
| R1 | 7.91 |

Example 2

A micro-vial was charged with the single crystal of the polynuclear metal complex A obtained in Production Example 3. After the addition of 50 µL of (−)-menthone having the structure represented by the following formula, the mixture was allowed to stand at 15 to 25° C. for 2 days to obtain a crystal structure analysis sample. The crystal structure analysis sample was subjected to X-ray crystal structure analysis.

Figure 7:
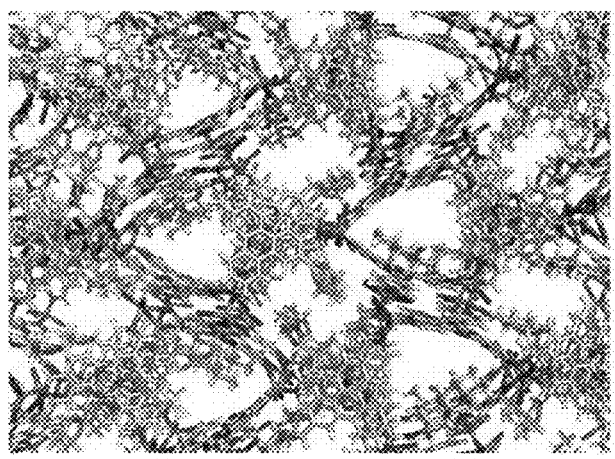
FIG. 7 is a view illustrating a polynuclear metal complex including (−)-menthone obtained in Example 2.

Table 3 shows the crystallographic data, and FIG. 7 illustrates the crystal structure.

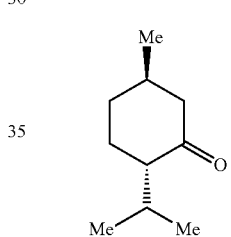

TABLE 3

| Crystal system | Orthorhombic |
| --- | --- |
| Space group | $P2_12_12_1$ |
| a (Å) | 13.951 (2) |
| b (Å) | 28.809 (3) |
| c (Å) | 44.682 (5) |
| α (°) | 90 |
| β (°) | 90 |
| γ (°) | 90 |
| Z | 4 |
| R1 | 7.71 |

Example 3

A micro-vial was charged with the single crystal of the polynuclear metal complex A obtained in Production Example 3. After the addition of 50 µL of (+)-menthone having the structure represented by the following formula, the mixture was allowed to stand at 15 to 25° C. for 2 days to obtain a crystal structure analysis sample. The crystal structure analysis sample was subjected to X-ray crystal structure analysis.

Figure 8:
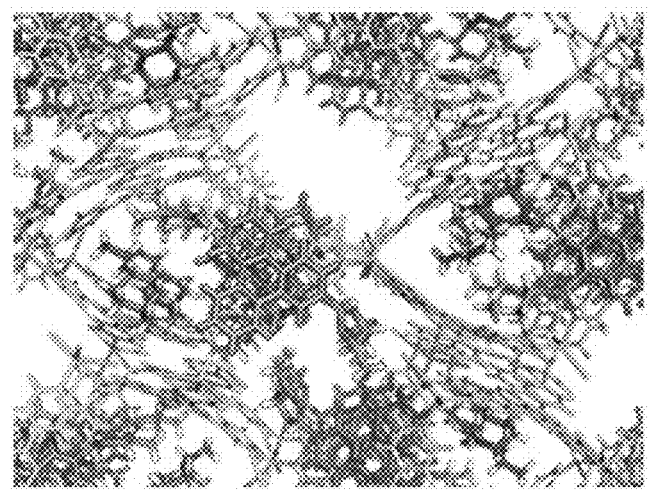
FIG. 8 is a view illustrating a polynuclear metal complex including (+)-menthone obtained in Example 3.

Table 4 shows the crystallographic data, and FIG. 8 illustrates the crystal structure.

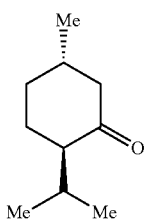

TABLE 4

| Crystal system | Orthorhombic |
| --- | --- |
| Space group | P2$_1$2$_1$2$_1$ |
| a (Å) | 13.960 (3) |
| b (Å) | 28.823 (6) |
| c (Å) | 44.262 (8) |
| α (°) | 90 |
| β (°) | 90 |
| γ (°) | 90 |
| Z | 4 |
| R1 | 8.49 |

Example 4

A micro-vial was charged with the single crystal of the polynuclear metal complex A obtained in Production Example 3. After the addition of 50 μL of (R)-1,3-dimethylpyrrolidine-2,5-dione having the structure represented by the following formula, the mixture was allowed to stand at 15 to 25° C. for 7 days to obtain a crystal structure analysis sample. The crystal structure analysis sample was subjected to X-ray crystal structure analysis.

Figure 9:
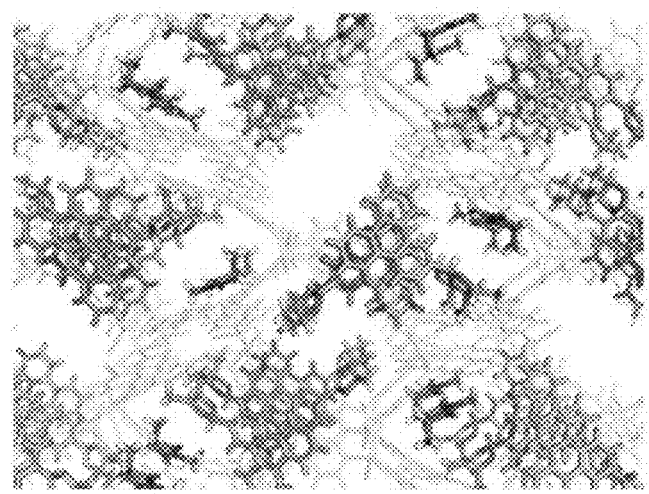
FIG. 9 is a view illustrating a polynuclear metal complex including (R)-1,3-dimethylpyrrolidine-2,5-dione obtained in Example 4.

Table 5 shows the crystallographic data, and FIG. 9 illustrates the crystal structure.

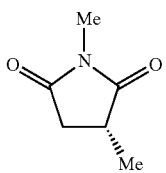

TABLE 5

| Crystal system | Orthorhombic |
| --- | --- |
| Space group | P2$_1$2$_1$2$_1$ |
| a (Å) | 13.989 (2) |
| b (Å) | 28.651 (4) |
| c (Å) | 44.397 (6) |
| α (°) | 90 |
| β (°) | 90 |
| γ (°) | 90 |
| Z | 4 |
| R1 | 6.90 |

Production Example 4

Preparation of Ligand Solution 6.3 mg of 2,4,6-tris(4-pyridyl)-1,3,5-triazine (TPT) and 32.8 mg of (4S,5S)-4,5-dimethyl-2-(triphenylen-2-yl)-1,3-dioxolane were dissolved in a nitrobenzene/methanol (4 mL/1 mL) mixture to obtain a ligand solution.

Production Example 5

Synthesis of Single Crystal of Porous Compound

The ligand solution obtained in Production Example 4 was put in a test tube (diameter: 15 mm, height: 12 cm), and 0.5 mL of methanol was slowly added to the 1.5 ligand solution. The metal ion-containing solution obtained in Production Example 2 was slowly added to the methanol layer so as to form an additional layer.

The solutions were allowed to stand at 15 to 25° C. for 7 days to obtain crystals of a polynuclear metal complex B. After removing the supernatant liquid by decantation, cyclohexane was poured into the mixture. This operation was repeated to replace the solvent with cyclohexane. The crystals were allowed to stand at room temperature for 5 days in a state in which the crystals were immersed in 10 mL of cyclohexane to saturate the pores of the crystals with cyclohexane.

A single crystal was then selected, and subjected to X-ray crystal structure analysis.

Figure 10:
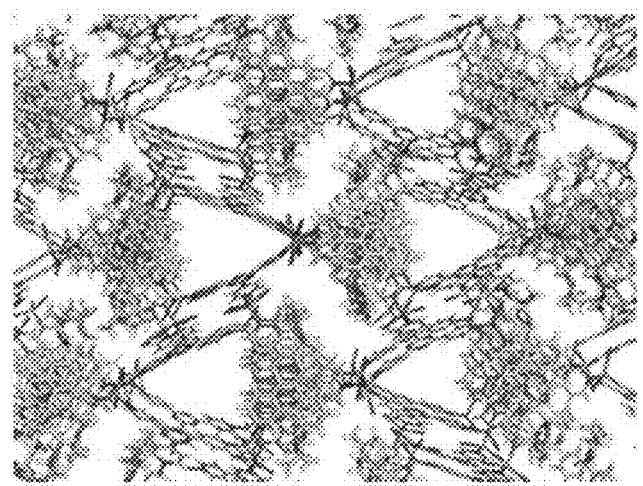
FIG. 10 is a view illustrating a polynuclear metal complex used in Examples 5 to 8.

Table 6 shows the crystallographic data, and FIG. 10 illustrates the crystal structure.

TABLE 6

| Crystal system | Orthorhombic |
| --- | --- |
| Space group | P2$_1$2$_1$2$_1$ |
| a (Å) | 13.7047 (6) |
| b (Å) | 28.5239 (9) |
| c (Å) | 44.7839 (19) |
| α (°) | 90 |
| β (°) | 90 |
| γ (°) | 90 |
| Z | 4 |
| R1 | 5.81 |

Example 5

A micro-vial was charged with the single crystal of the polynuclear metal complex B obtained in Production Example 5. After the addition of 50 μL of (−)-menthone having the structure represented by the following formula, the mixture was allowed to stand at 15 to 25° C. for 2 days to obtain a crystal structure analysis sample. The crystal structure analysis sample was subjected to X-ray crystal structure analysis.

Figure 11:
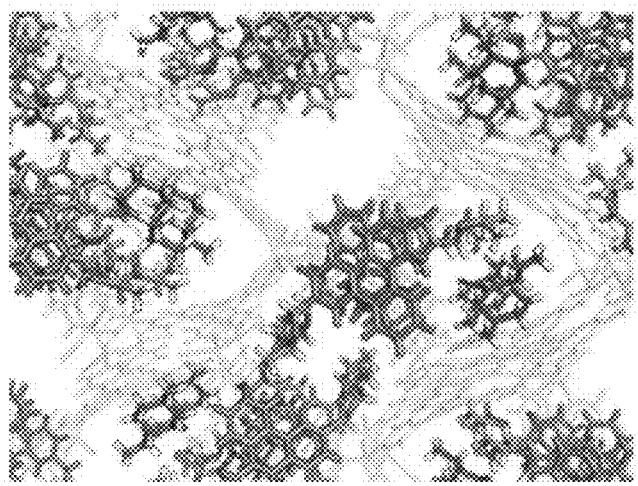
FIG. 11 is a view illustrating a polynuclear metal complex including (+)-menthone obtained in Example 5.

Table 7 shows the crystallographic data, and FIG. 11 illustrates the crystal structure.

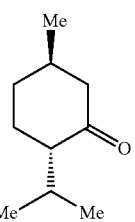

TABLE 7

| Crystal system | Orthorhombic |
| --- | --- |
| Space group | P2$_1$2$_1$2$_1$ |
| a (Å) | 13.9817 (12) |
| b (Å) | 28.988 (2) |

TABLE 7-continued

| | |
|---|---|
| c (Å) | 44.391 (4) |
| α (°) | 90 |
| β (°) | 90 |
| γ (°) | 90 |
| Z | 4 |
| R1 | 7.37 |

Example 6

A micro-vial was charged with the single crystal of the polynuclear metal complex B obtained in Production Example 5. After the addition of 50 μL of (+)-menthone having the structure represented by the following formula, the mixture was allowed to stand at 15 to 25° C. for 2 days to obtain a crystal structure analysis sample. The crystal structure analysis sample was subjected to X-ray crystal structure analysis.

Figure 12:
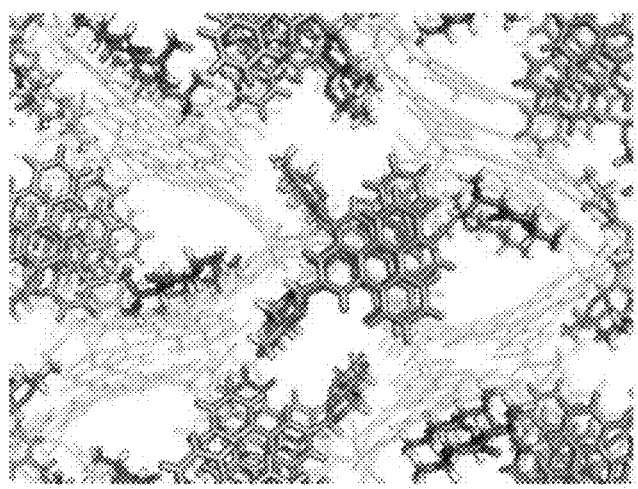
FIG. 12 is a view illustrating, a polynuclear metal complex including (+)-menthone obtained in Example 6.

Table 8 shows the crystallographic data, and FIG. 12 illustrates the crystal structure.

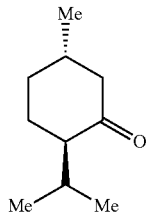

TABLE 8

| | |
|---|---|
| Crystal system | Orthorhombic |
| Space group | P2$_1$2$_1$2$_1$ |
| a (Å) | 13.960 (3) |
| b (Å) | 28.823 (6) |
| c (Å) | 44.262 (8) |
| α (°) | 90 |
| β (°) | 90 |
| γ (°) | 90 |
| Z | 4 |
| R1 | 8.49 |

Example 7

A micro-vial was charged with the single crystal of the polynuclear metal complex B obtained in Production Example 5. After the addition of 5 μL of a solution (1 mg/mL) prepared by dissolving (+)-dimethyl L-tartrate having the structure represented by the following formula in methylene chloride, and 45 μL of cyclohexane, the solvent was slowly evaporated at 50° C. over 2 days to obtain a crystal structure analysis sample. The crystal structure analysis sample was subjected to X-ray crystal structure analysis.

Figure 13:
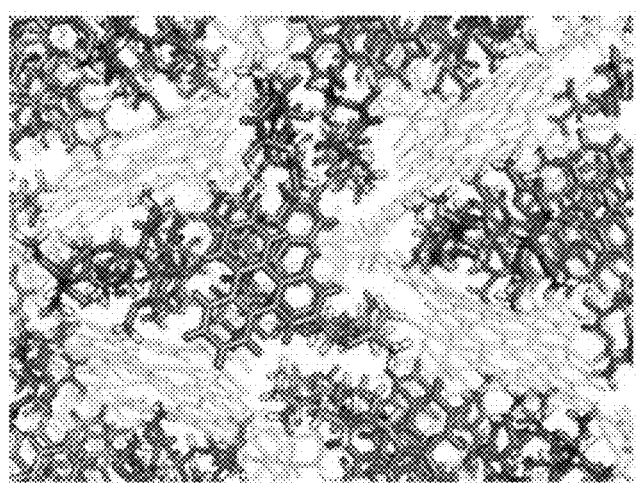
FIG. 13 is a view illustrating, a polynuclear metal complex including (+)-dimethyl L-tartrate obtained in Example 7.

Table 9 shows the crystallographic data, and FIG. 13 illustrates the crystal structure.

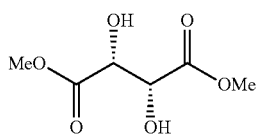 [SMILES: COC(=O)[C@H](O)[C@@H](O)C(=O)OC]

TABLE 9

| | |
|---|---|
| Crystal system | Orthorhombic |
| Space group | P2$_1$2$_1$2$_1$ |
| a (Å) | 13.9105 (13) |
| b (Å) | 28.652 (3) |
| c (Å) | 44.885 (4) |
| α (°) | 90 |
| β (°) | 90 |
| γ (°) | 90 |
| Z | 4 |
| R1 | 6.36 |

Example 8

About 20 μL of a solution (5 mg/mL) prepared by dissolving a racemic mixture of 2-bromo-1-phenylethanol in hexane was subjected to analytical liquid chromatography (column: CHIRALPAK IC, hexane/ethanol=99:1) to collect a fraction eluted at around 11.7 minutes.

A micro-vial was charged with the resulting fraction. After evaporating the solvent, the residue was dissolved in 5 μL of 1,2-dichloroethane and 45 μL of cyclohexane. After the addition of the single crystal of the polynuclear metal complex B obtained in Production Example 5 to the resulting solution, the solvent was slowly evaporated at 50° C. over 2 days to obtain a crystal structure analysis sample. The crystal structure analysis sample was subjected to X-ray crystal structure analysis. As a result, it was found that the compound was the (R)-isomer shown below.

Figure 14:
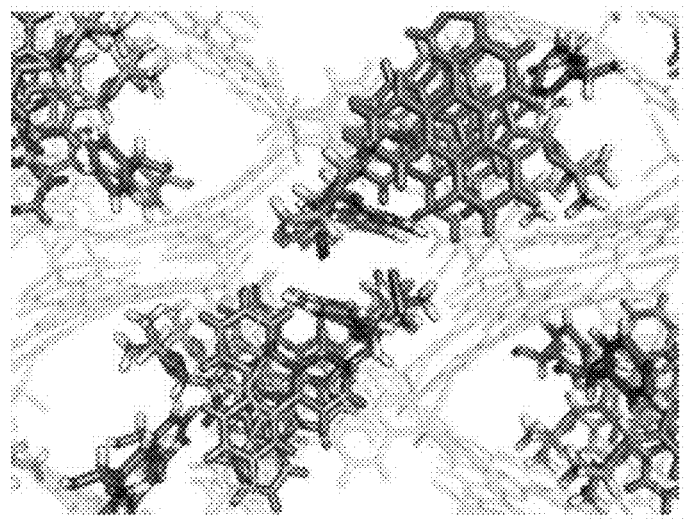
FIG. 14 is a view illustrating a polynuclear metal complex including (R)-2-bromo-1-phenylethanol obtained in Example 8.

Table 10 shows the crystallographic data, and FIG. 14 illustrates the crystal structure.

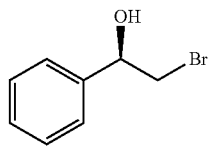

TABLE 10

| | |
|---|---|
| Crystal system | Orthorhombic |
| Space group | P2$_1$2$_1$2$_1$ |
| a (Å) | 13.9239 (19) |
| b (Å) | 28.645 (4) |
| c (Å) | 44.158 (6) |
| α (°) | 90 |
| β (°) | 90 |
| γ (°) | 90 |
| Z | 4 |
| R1 | 7.34 |

Example 9

About 20 μL of a solution (5 mg/mL) prepared by dissolving a racemic mixture of 2-bromo-1-phenylethanol in hexane was subjected to analytical liquid chromatography (column: CHIRALPAK IC, hexane/ethanol=99:1) to collect a fraction eluted at around 12.3 minutes.

A micro-vial was charged with the resulting fraction. After evaporating the solvent, the residue was dissolved in 5 μL of 1,2-dichloroethane and 45 μL of cyclohexane. After the addition of the single crystal of the polynuclear metal complex A obtained in Production Example 3 to the resulting solution, the solvent was slowly evaporated at 50° C.

over 2 days to obtain a crystal structure analysis sample. The crystal structure analysis sample was subjected to X-ray crystal structure analysis. As a result, it was found that the compound was the (S)-isomer shown below.

Figure 15:
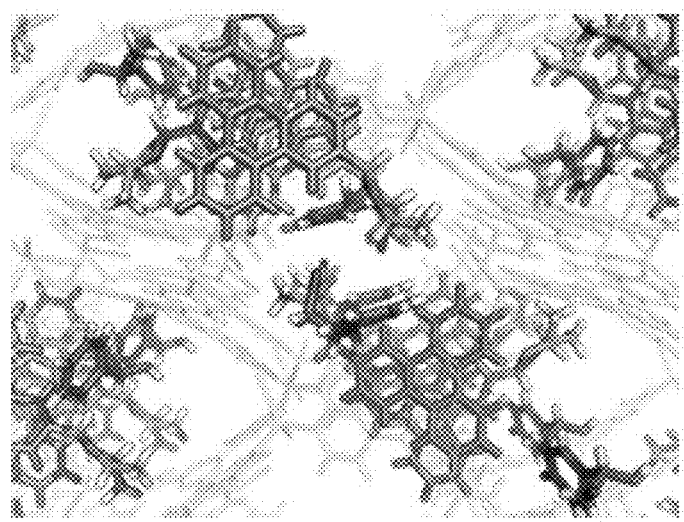
FIG. 15 is a view illustrating a polynuclear metal complex including (S)-2-bromo-1-phenylethanol obtained in Example 9.

Table 11 shows the crystallographic data, and FIG. 15 illustrates the crystal structure.

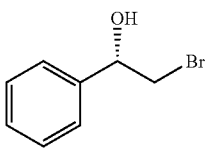

TABLE 11

| Crystal system | Orthorhombic |
|---|---|
| Space group | $P2_12_12_1$ |
| a (Å) | 13.8958 (3) |
| b (Å) | 28.6671 (7) |
| c (Å) | 43.9979 (11) |
| α (°) | 90 |
| β (°) | 90 |
| γ (°) | 90 |
| Z | 4 |
| R1 | 8.33 |

REFERENCE SIGNS LIST

1: Crystal plane X
2: Crystal plane Y
3: Pore
4: Extension direction of pore

The invention claimed is:

1. A method for preparing a crystal structure analysis sample for determining an absolute configuration of a chiral compound, the method comprising bringing a single crystal of a porous compound into contact with a solvent solution that comprises a chiral compound for which the absolute configuration is to be determined, to prepare a crystal structure analysis sample, the single crystal of the porous compound comprising a three-dimensional framework, and either or both of pores and voids that are defined by the three-dimensional framework, and are three-dimensionally arranged in an ordered manner, the three-dimensional framework being formed by one molecular chain or two or more molecular chains, and a framework-forming compound, and comprising a chiral substituent of which the absolute configuration is known, the crystal structure analysis sample having a structure in which molecules of the chiral compound are arranged in either or both of the pores and the voids of the single crystal in an ordered manner.

2. The method for preparing a crystal structure analysis sample according to claim 1, wherein the porous compound is a polynuclear metal complex that comprises a ligand having two or more coordinating moieties, a metal ion that serves as a center metal, and the framework-forming compound that comprises the chiral substituent of which the absolute configuration is known.

3. The method for preparing a crystal structure analysis sample according to claim 2, wherein the ligand having two or more coordinating moieties is a tridentate ligand represented by a formula (1),

(1)

wherein Ar is a substituted or unsubstituted trivalent aromatic group, $X^1$ to $X^3$ are independently a divalent organic group, or a single bond that directly bonds Ar and or $Y^1$, $Y^2$, or $Y^3$, and $Y^1$ to $Y^3$ are independently a monovalent organic group having a coordinating moiety.

4. The method for preparing a crystal structure analysis sample according to claim 2, wherein the metal ion that serves as the center metal is an ion of a metal among the metals that respectively belong to Groups 8 to 12 in the periodic table.

5. The method for preparing a crystal structure analysis sample according to claim 1, wherein the single crystal is brought into contact with the solvent solution that comprises the chiral compound by immersing the single crystal in the solvent solution that comprises the chiral compound.

* * * * *